(12) United States Patent
Savarino

(10) Patent No.: US 9,095,539 B2
(45) Date of Patent: Aug. 4, 2015

(54) ANTI-ADHESIN BASED PASSIVE IMMUNOPROPHYLACTIC

(75) Inventor: Stephen J. Savarino, Kensington, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 253 days.

(21) Appl. No.: 12/822,429

(22) Filed: Jun. 24, 2010

(65) Prior Publication Data
US 2010/0297141 A1 Nov. 25, 2010

Related U.S. Application Data

(62) Division of application No. 11/439,061, filed on May 23, 2006, now abandoned.

(60) Provisional application No. 60/683,787, filed on May 24, 2005.

(51) Int. Cl.
| | |
|---|---|
| C12N 1/20 | (2006.01) |
| G01N 33/569 | (2006.01) |
| A61K 39/00 | (2006.01) |
| A61K 39/02 | (2006.01) |
| A61K 39/108 | (2006.01) |
| A61K 39/40 | (2006.01) |
| C07K 16/12 | (2006.01) |

(52) U.S. Cl.
CPC .......... A61K 39/0258 (2013.01); C07K 16/1232 (2013.01); A61K 2039/505 (2013.01); C07K 2316/96 (2013.01)

(58) Field of Classification Search
CPC ............. C12N 15/70; G01N 33/56916; A61K 39/0258
See application file for complete search history.

(56) References Cited

U.S. PATENT DOCUMENTS

5,914,114 A * 6/1999 Cassels ...................... 424/241.1

OTHER PUBLICATIONS

Barman et al., Veterinarski Arhiv, 2001; 71(6): 381-387.*
Anantha et al., Infection and Immunity, Dec. 2004; 72(12): 7190-7201.*
Kleppe et al. (Tidsskr nor Laegeforen, Sep. 30, 2001; 121(23):2717-20.*
Hoppner (Horm Re. 2002, 58 Suppl. 3:7-15.*
Bowie et al. (Science, 1990, 257:1306-1310).*

* cited by examiner

*Primary Examiner* — Gary Nickol
*Assistant Examiner* — Lakia Tongue
(74) *Attorney, Agent, or Firm* — Albert M. Churilla; Ning Yang

(57) ABSTRACT

The invention relates to an immunogenic composition and method of the immunogenic composition for the production and administration of a passive immunoprophylactic against enterotoxigenic *Escherichia coli*. The immunoprophylactic is made collecting anti-adhesin in the colostrum or milk of vaccinated domesticated animals such as cows. The immunoprophylactic is administered either as a dietary supplement or in capsular or tablet form.

17 Claims, 6 Drawing Sheets

| Polypeptide Sequence | Major Subunit | Fimbriae | SEQ ID No. |
|---|---|---|---|
| VEKNITVTASVDPVIDLLQA | CfaB | CFA/I | 1 |
| VEKNITVTASVDPTIDILQA | CsfA | CS4 | 2 |
| VEKNITVTASVDPTIDILQA | CsuA1 | CS14 | 3 |
| VEKNITVTASVDPTIDILQA | CsuA2 | CS14 | 4 |
| VEKTISVTASVDPTVDLLQS | CooA | CS1 | 5 |
| VEKTISVTASVDPTVDLLQS | CosA | PCF071 | 6 |
| VEKNITVRASVDPKLDLLQA | CsbA | CS17 | 7 |
| VEKNITVRASVDPKLDLLQA | CsdA | CS19 | 8 |
| AEKNITVTASVDPTIDLMQS | CotB | CS2 | 9 |
| VQKDITVTANVDTTLEMLSA | CblA | Bcep | 38 |
| VQKDITVTANIDSTLELLQA | TsaB | Styp | 39 |

UZKxUTUxAxUDxxUDUUxx

FIG. 1

SEQUENCE LISTING

```
<160> NUMBER OF SEQ ID NOS: 37

<210> SEQ ID NO 1
<211> LENGTH: 20
<212> TYPE: PRT
<213> ORGANISM: Escherichia coli

<400> SEQUENCE: 1

Val Glu Lys Asn Ile Thr Val Thr Ala Ser Val Asp Pro Val Ile Asp
1               5                   10                  15

Leu Leu Gln Ala
            20

<210> SEQ ID NO 2
<211> LENGTH: 20
<212> TYPE: PRT
<213> ORGANISM: Escherichia coli
```

```
<400> SEQUENCE: 2

Val Glu Lys Asn Ile Thr Val Thr Ala Ser Val Asp Pro Thr Ile Asp
1               5                   10                  15

Ile Leu Gln Ala
            20

<210> SEQ ID NO 3
<211> LENGTH: 20
<212> TYPE: PRT
<213> ORGANISM: Escherichia coli

<400> SEQUENCE: 3

Val Glu Lys Asn Ile Thr Val Thr Ala Ser Val Asp Pro Thr Ile Asp
1               5                   10                  15

Ile Leu Gln Ala
            20

<210> SEQ ID NO 4
<211> LENGTH: 20
<212> TYPE: PRT
<213> ORGANISM: Escherichia coli

<400> SEQUENCE: 4

Val Glu Lys Asn Ile Thr Val Thr Ala Ser Val Asp Pro Thr Ile Asp
1               5                   10                  15

Ile Leu Gln Ala
            20

<210> SEQ ID NO 5
<211> LENGTH: 20
<212> TYPE: PRT
<213> ORGANISM: Escherichia coli

<400> SEQUENCE: 5

Val Glu Lys Thr Ile Ser Val Thr Ala Ser Val Asp Pro Thr Val Asp
1               5                   10                  15

Leu Leu Gln Ser
            20

<210> SEQ ID NO 6
<211> LENGTH: 20
<212> TYPE: PRT
<213> ORGANISM: Escherichia coli

<400> SEQUENCE: 6

Val Glu Lys Thr Ile Ser Val Thr Ala Ser Val Asp Pro Thr Val Asp
1               5                   10                  15

Leu Leu Gln Ser
            20

<210> SEQ ID NO 7
<211> LENGTH: 20
<212> TYPE: PRT
<213> ORGANISM: Escherichia coli

<400> SEQUENCE: 7

Val Glu Lys Asn Ile Thr Val Arg Ala Ser Val Asp Pro Lys Leu Asp
1               5                   10                  15

Leu Leu Gln Ala
            20
```

-continued

<210> SEQ ID NO 8
<211> LENGTH: 20
<212> TYPE: PRT
<213> ORGANISM: Escherichia coli

<400> SEQUENCE: 8

Val Glu Lys Asn Ile Thr Val Arg Ala Ser Val Asp Pro Lys Leu Asp
1               5                   10                  15

Leu Leu Gln Ala
            20

<210> SEQ ID NO 9
<211> LENGTH: 19
<212> TYPE: PRT
<213> ORGANISM: Escherichia coli

<400> SEQUENCE: 9

Ala Glu Lys Asn Ile Thr Val Thr Ala Ser Val Asp Pro Thr Ile Asp
1               5                   10                  15

Leu Met Gln

<210> SEQ ID NO 10
<211> LENGTH: 4
<212> TYPE: PRT
<213> ORGANISM: Escherichia coli

<400> SEQUENCE: 10

Asp Asn Lys Gln
1

<210> SEQ ID NO 11
<211> LENGTH: 360
<212> TYPE: PRT
<213> ORGANISM: Escherichia coli

<400> SEQUENCE: 11

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

-continued

```
Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Ala Gly Lys
        275                 280                 285

Asn Leu Thr Pro Thr Asn Gly Gln Ala Leu Asn Ile Asn Thr Ala Ser
            290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu
            355                 360

<210> SEQ ID NO 12
<211> LENGTH: 5
<212> TYPE: PRT
<213> ORGANISM: Escherichia coli

<400> SEQUENCE: 12

Gly Asp Asn Lys Gln
1               5

<210> SEQ ID NO 13
<211> LENGTH: 6
<212> TYPE: PRT
<213> ORGANISM: Escherichia coli

<400> SEQUENCE: 13

Gly Asp Asn Lys Gln Gly
1               5

<210> SEQ ID NO 14
<211> LENGTH: 57
<212> TYPE: DNA
<213> ORGANISM: Escherichia coli

<400> SEQUENCE: 14
tcgacaataa acaagtagag aaaaatatta ctgtaacagc tagtgttgat ccttagc    57

<210> SEQ ID NO 15
<211> LENGTH: 57
<212> TYPE: DNA
<213> ORGANISM: Escherichia coli

<400> SEQUENCE: 15
tcgagctaag gatcaacact agctgttaca gtaatatttt tctctacttg tttattg    57
```

```
<210> SEQ ID NO 16
<211> LENGTH: 45
<212> TYPE: DNA
<213> ORGANISM: Escherichia coli

<400> SEQUENCE: 16
cgcggggaat tccatatgaa taaaatttta tttatttta cattg            45

<210> SEQ ID NO 17
<211> LENGTH: 36
<212> TYPE: DNA
<213> ORGANISM: Escherichia coli

<400> SEQUENCE: 17
cgcccgctcg agttgcaaaa gatcaatcac aggatc                      36

<210> SEQ ID NO 18
<211> LENGTH: 1080
<212> TYPE: DNA
<213> ORGANISM: Escherichia coli

<400> SEQUENCE: 18
atgaataaaa ttttatttat ttttacattg ttttttcct cagggttttt tacatttgcc     60
gtatcggcag ataaaaatcc cggaagtgaa acatgactaa atactattgg tccccatgac   120
agggggggat cttcccccat atataatatc ttaaattcct atcttacagc atacaatgga   180
agccatcatc tgtatgatag gatgagtttt ttatgtttgt cttctcaaaa tacactgaat   240
ggagcatgcc caagcagtga tgcccctggc actgctacaa ttgatggcga acaaaatata   300
acattacaat ttacggaaaa aagaagtcta attaaaagag aactgcaaat taaaggctat   360
aaacaatttt tgttcaaaaa tgctaattgc ccatctaaac tagcacttaa ctcatctcat   420
tttcaatgta atagagaaca agcttcaggt gctactttat cgttatacat accagctggt   480
gaattaaata aattaccttt tgggggggtc tggaatgccg ttctgaagct aaatgtaaaa   540
agacgatatg atacaaccta tgggacttac actataaaca tcacagttaa tttaactgat   600
aagggaaata ttcagatatg gttaccacag ttcaaaagta acgctcgtgt cgatcttaac   660
ttgcgtccaa ctggtggtgg tacatatatc ggaagaaatt ctgttgatat gtgcttttat   720
gatggatata gtactaacag cagctcttta gagataagat ttcaggatga taattctaaa   780
tctgatggaa aattttatct aaagaaaata aatgatgact ccaaagaact tgtatacact   840
ttgtcacttc tcctggcagg taaaaattta acaccaacaa atggacaggc attaaatatt   900
aacactgctt ctctggaaac aaactggaat agaattacag ctgtcaccat gccagaaatc   960
agtgttccgg tgttgtgttg gcctggacgt ttgcaattgg atgcaaaagt gaaaaatccc  1020
gaggctggac aatatatggg gaatattaaa attactttca caccaagtag tcaaacactc  1080

<210> SEQ ID NO 19
<211> LENGTH: 1089
<212> TYPE: DNA
<213> ORGANISM: Escherichia coli

<400> SEQUENCE: 19
atgaaaaaga tatttatttt tttgtctatc atattttctg cggtggtcag tgccgggcga     60
tacccggaaa ctacagtagg taatctgacg aagagttttc aagcccctcg tcaggataga   120
agcgtacaat caccaatata taacatcttt acgaatcatg tggctggata tagtttgagt   180
cataacttat atgacaggat tgttttttta tgtacatcct cgtcgaatcc ggttaatggt   240
```

-continued

```
gcttgcccaa cccttggaac atctggagtt caatacggta ctacaaccat aaccttgcag    300
tttacagaaa aaagaagtct gataaaaaga aatattaatc ttgcaggtaa taagaaacca    360
atatgggaga atcagagttg cgacactagc aatctaatgg tgttgaattc gaagtcttgg    420
tcctgtgggc attacggaaa tgctaacgga acacttctaa atctgtatat ccctgcagga    480
gaaatcaaca aattgccttt tggagggata tgggaggcaa ctctgatctt acgcttatca    540
agatatggcg aagtcagtag caccccattac ggcaattata ccgtaaatat tacggttgat    600
ttaactgata aaggtaatat tcaggtatgg cttccagggt ttcacagcaa cccgcgtgta    660
gacctgaatc tgcaccctat cggtaattat aaatatagtg gtagtaattc actcgacatg    720
tgtttctatg atggatatag tacaaacagt gatagcatgg aataaaagtt ccaggatgat    780
aatcctacct attcatctga atataatctt tataagatag ggggcactga aaaattaccc    840
tatgctgttt cactgcttat gggagaaaaa atattttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaattta                                                            1089

<210> SEQ ID NO 20
<211> LENGTH: 63
<212> TYPE: DNA
<213> ORGANISM: Escherichia coli

<400> SEQUENCE: 20
gtagagaaaa atattactgt aacagctagt gttgatcctg tgattgatct tttgcaactc     60
gag                                                                   63

<210> SEQ ID NO 21
<211> LENGTH: 63
<212> TYPE: DNA
<213> ORGANISM: Escherichia coli

<400> SEQUENCE: 21
gtcgaaaaaa atattactgt gagggcaagt gttgacccta aacttgatct tctgcaactc     60
gag                                                                   63

<210> SEQ ID NO 22
<211> LENGTH: 363
<212> TYPE: PRT
<213> ORGANISM: Escherichia coli

<400> SEQUENCE: 22

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
                20                  25                  30

Phe Gln Ala Pro Arg Gln Asp Arg Ser Val Gln Ser Pro Ile Tyr Asn
            35                  40                  45

Ile Phe Thr Asn His Val Ala Gly Tyr Ser Leu Ser His Asn Leu Tyr
        50                  55                  60

Asp Arg Ile Val Phe Leu Cys Thr Ser Ser Asn Pro Val Asn Gly
65                  70                  75                  80

Ala Cys Pro Thr Leu Gly Thr Ser Gly Val Gln Tyr Gly Thr Thr Thr
                85                  90                  95
```

```
Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Thr Ser Asn Leu Met Val Leu Asn Ser Lys Ser Trp Ser Cys Gly His
    130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205

Val Trp Leu Pro Gly Phe His Ser Asn Pro Arg Val Asp Leu Asn Leu
    210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Tyr Ser Ser Glu Tyr Asn Leu Tyr Lys
            260                 265                 270

Ile Gly Gly Thr Glu Lys Leu Pro Tyr Ala Val Ser Leu Leu Met Gly
        275                 280                 285

Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu
        355                 360

<210> SEQ ID NO 23
<211> LENGTH: 1176
<212> TYPE: DNA
<213> ORGANISM: Escherichia coli

<400> SEQUENCE: 23
atgaataaaa ttttatttat ttttacattg ttttttttctt cagggttttt tacatttgcc      60
gtatcggcag ataaaaatcc cggaagtgaa aacatgacta atactattgg tccccatgac     120 aggggggat cttcccccat atataatatc ttaaattcct atcttacagc atacaatgga      180
agccatcatc tgtatgatag gatgagtttt ttatgtttgt cttctcaaaa tacactgaat     240
ggagcatgcc caagcagtga tgcccctggc actgctacaa ttgatggcga acaaatata     300 acattacaat ttacggaaaa agaagtctta attaaaagag aactgcaaat taaaggctat     360
aaacaatttt tgttcaaaaa tgctaattgc ccatctaaac tagcacttaa ctcatctcat     420
tttcaatgta atagagaaca agcttcaggt gctactttat cgttatacat accagctggt     480
gaattaaata attaccttt tgggggggtc tggaatgccg ttctgaagct aaatgtaaaa     540
agacgatatg atacaaccta tgggacttac actataaaca tcacagttaa tttaactgat     600
```

```
aagggaaaata ttcagatatg gttaccacag ttcaaaagta acgctcgtgt cgatcttaac    660
ttgcgtccaa ctggtggtgg tacatatatc ggaagaaatt ctgttgatat gtgctttat     720 gatggatata gtactaacag cagctctta gagataagat ttcaggatga taattctaaa     780
tctgatggaa aattttatct aaagaaaata aatgatgact ccaaagaact tgtatacact    840
ttgtcacttc tcctggcagg taaaaattta acaccaacaa atggacaggc attaaatatt    900
aacactgctt ctctggaaac aaactggaat agaattacag ctgtcaccat gccagaaatc    960
agtgttccgg tgttgtgttg gcctggacgt ttgcaattgg atgcaaaagt gaaaaatccc   1020
gaggctggac aatatatggg gaatattaaa attactttca caccaagtag tcaaacactc   1080
gacaataaac aagtagagaa aaatattact gtaacagcta gtgttgatcc tgtgattgat   1140
cttttgcaac tcgagcacca ccaccaccac cactga                             1176
```

<210> SEQ ID NO 24
<211> LENGTH: 391
<212> TYPE: PRT
<213> ORGANISM: Escherichia coli

<400> SEQUENCE: 24

```
Met Asn Lys Ile Leu Phe Ile Phe Thr Leu Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270
```

Asp Ser Lys Glu Leu Val Tyr Thr Leu Ser Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Val Ile Asp Leu Leu Gln Leu
    370                 375                 380

Glu His His His His His His
385                 390

<210> SEQ ID NO 25
<211> LENGTH: 1185
<212> TYPE: DNA
<213> ORGANISM: Escherichia coli

<400> SEQUENCE: 25
atgaaaaaga tatttatttt tttgtctatc atattttctg cggtggtcag tgccgggcga      60
tacccggaaa ctacagtagg taatctgacg aagagttttc aagcccctcg tcaggataga    120
agcgtacaat caccaatata taacatcttt acgaatcatg tggctggata gtttgagt       180 cataacttat atgacaggat tgtttttta tgtacatcct cgtcgaatcc ggttaatggt     240
gcttgcccaa cccttggaac atctggagtt caatacggta ctacaaccat aaccttgcag    300
tttacagaaa aaagaagtct gataaaaaga aatattaatc ttgcaggtaa taagaaacca    360
atatgggaga atcagagttg cgacactagc aatctaatgg tgttgaattc gaagtcttgg    420
tcctgtgggc attacggaaa tgctaacgga acacttctaa atctgtatat ccctgcagga    480
gaaatcaaca aattgccttt tggagggata tgggaggcaa ctctgatctt acgcttatca    540
agatatggcg aagtcagtag cacccattac ggcaattata ccgtaaatat tacggttgat    600
ttaactgata aaggtaatat tcaggtatgg cttccagggt ttcacagcaa cccgcgtgta    660
gacctgaatc tgcaccctat cggtaattat aaatatagtg gtagtaattc actcgacatg    720
tgtttctatg atggatatag tacaaacagt gatagcatgg taataaagtt ccaggatgat    780
aatcctacct attcatctga atataatctt tataagatag ggggcactga aaaattaccc    840
tatgctgttt cactgcttat gggagaaaaa atatttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttag acaataaaca agtcgaaaaa aatattactg tgagggcaag tgttgaccct   1140
aaacttgatc ttctgcaact cgagcaccac caccaccacc actga                   1185

<210> SEQ ID NO 26
<211> LENGTH: 376
<212> TYPE: PRT
<213> ORGANISM: Escherichia coli

<400> SEQUENCE: 26

| Gly | Arg | Tyr | Pro | Glu | Thr | Thr | Val | Gly | Asn | Leu | Thr | Lys | Ser | Phe | Gln |
|---|---|---|---|---|---|---|---|---|---|---|---|---|---|---|---|
| 1 | | | | 5 | | | | | 10 | | | | | 15 | |

| Ala | Pro | Arg | Gln | Asp | Arg | Ser | Val | Gln | Ser | Pro | Ile | Tyr | Asn | Ile | Phe |
| | | | 20 | | | | | 25 | | | | | 30 | | |

| Thr | Asn | His | Val | Ala | Gly | Tyr | Ser | Leu | Ser | His | Asn | Leu | Tyr | Asp | Arg |
| | | 35 | | | | | 40 | | | | | 45 | | | |

| Ile | Val | Phe | Leu | Cys | Thr | Ser | Ser | Asn | Pro | Val | Asn | Gly | Ala | Cys |
| | 50 | | | | | 55 | | | | 60 | | | | |

| Pro | Thr | Leu | Gly | Thr | Ser | Gly | Val | Gln | Tyr | Gly | Thr | Thr | Ile | Thr |
| 65 | | | | 70 | | | | | 75 | | | | | 80 |

| Leu | Gln | Phe | Thr | Glu | Lys | Arg | Ser | Leu | Ile | Lys | Arg | Asn | Ile | Asn | Leu |
| | | | | 85 | | | | | 90 | | | | | 95 | |

| Ala | Gly | Asn | Lys | Lys | Pro | Ile | Trp | Glu | Asn | Gln | Ser | Cys | Asp | Thr | Ser |
| | | | 100 | | | | | 105 | | | | | 110 | | |

| Asn | Leu | Met | Val | Leu | Asn | Ser | Lys | Ser | Trp | Ser | Cys | Gly | His | Tyr | Gly |
| | | 115 | | | | | 120 | | | | | 125 | | | |

| Asn | Ala | Asn | Gly | Thr | Leu | Leu | Asn | Leu | Tyr | Ile | Pro | Ala | Gly | Glu | Ile |
| | 130 | | | | | 135 | | | | 140 | | | | |

| Asn | Lys | Leu | Pro | Phe | Gly | Gly | Ile | Trp | Glu | Ala | Thr | Leu | Ile | Leu | Arg |
| 145 | | | | | 150 | | | | | 155 | | | | | 160 |

| Leu | Ser | Arg | Tyr | Gly | Glu | Val | Ser | Ser | Thr | His | Tyr | Gly | Asn | Tyr | Thr |
| | | | | 165 | | | | | 170 | | | | | 175 | |

| Val | Asn | Ile | Thr | Val | Asp | Leu | Thr | Asp | Lys | Gly | Asn | Ile | Gln | Val | Trp |
| | | | 180 | | | | | 185 | | | | | 190 | | |

| Leu | Pro | Gly | Phe | His | Ser | Asn | Pro | Arg | Val | Asp | Leu | Asn | Leu | His | Pro |
| | | 195 | | | | | 200 | | | | | 205 | | | |

| Ile | Gly | Asn | Tyr | Lys | Tyr | Ser | Gly | Ser | Asn | Ser | Leu | Asp | Met | Cys | Phe |
| | 210 | | | | | 215 | | | | 220 | | | | |

| Tyr | Asp | Gly | Tyr | Ser | Thr | Asn | Ser | Asp | Ser | Met | Val | Ile | Lys | Phe | Gln |
| 225 | | | | | 230 | | | | | 235 | | | | | 240 |

| Asp | Asp | Asn | Pro | Thr | Tyr | Ser | Ser | Glu | Tyr | Asn | Leu | Tyr | Lys | Ile | Gly |
| | | | | 245 | | | | | 250 | | | | | 255 | |

| Gly | Thr | Glu | Lys | Leu | Pro | Tyr | Ala | Val | Ser | Leu | Leu | Met | Gly | Glu | Lys |
| | | | 260 | | | | | 265 | | | | | 270 | | |

| Ile | Phe | Tyr | Pro | Val | Asn | Gly | Gln | Ser | Phe | Thr | Ile | Asn | Asp | Ser | Ser |
| | | 275 | | | | | 280 | | | | | 285 | | | |

| Val | Leu | Glu | Thr | Asn | Trp | Asn | Arg | Val | Thr | Ala | Val | Ala | Met | Pro | Glu |
| | 290 | | | | | 295 | | | | 300 | | | | |

| Val | Asn | Val | Pro | Val | Leu | Cys | Trp | Pro | Ala | Arg | Leu | Leu | Leu | Asn | Ala |
| 305 | | | | | 310 | | | | | 315 | | | | | 320 |

| Asp | Val | Asn | Ala | Pro | Asp | Ala | Gly | Gln | Tyr | Ser | Gly | Gln | Ile | Tyr | Ile |
| | | | | 325 | | | | | 330 | | | | | 335 | |

| Thr | Phe | Thr | Pro | Ser | Val | Glu | Asn | Leu | Asp | Asn | Lys | Gln | Val | Glu | Lys |
| | | | 340 | | | | | 345 | | | | | 350 | | |

| Asn | Ile | Thr | Val | Arg | Ala | Ser | Val | Asp | Pro | Lys | Leu | Asp | Leu | Leu | Gln |
| | | 355 | | | | | 360 | | | | | 365 | | | |

| Leu | Glu | His | His | His | His | His |
| | 370 | | | | 375 | |

<210> SEQ ID NO 27
<211> LENGTH: 361
<212> TYPE: PRT
<213> ORGANISM: Escherichia coli

<400> SEQUENCE: 27

```
Met Asn Lys Ile Leu Phe Ile Phe Thr Leu Phe Phe Ser Ser Val Leu
1               5                   10                  15

Phe Thr Phe Ala Val Ser Ala Asp Lys Ile Pro Gly Asp Glu Ser Ile
            20                  25                  30

Thr Asn Ile Phe Gly Pro Arg Asp Arg Asn Glu Ser Ser Pro Lys His
        35                  40                  45

Asn Ile Leu Asn Asn His Ile Thr Ala Tyr Ser Glu Ser His Thr Leu
    50                  55                  60

Tyr Asp Arg Met Thr Phe Leu Cys Leu Ser Ser His Asn Thr Leu Asn
65                  70                  75                  80

Gly Ala Cys Pro Thr Ser Glu Asn Pro Ser Ser Ser Val Ser Gly
                85                  90                  95

Glu Thr Asn Ile Thr Leu Gln Phe Thr Glu Lys Arg Ser Leu Ile Lys
                100                 105                 110

Arg Glu Leu Gln Ile Lys Gly Tyr Lys Gln Leu Leu Phe Lys Ser Val
            115                 120                 125

Asn Cys Pro Ser Gly Leu Thr Leu Asn Ser Ala His Phe Asn Cys Asn
130                 135                 140

Lys Asn Ala Ala Ser Gly Ala Ser Leu Tyr Leu Tyr Ile Pro Ala Gly
145                 150                 155                 160

Glu Leu Lys Asn Leu Pro Phe Gly Gly Ile Trp Asp Ala Thr Leu Lys
                165                 170                 175

Leu Arg Val Lys Arg Arg Tyr Ser Glu Thr Tyr Gly Thr Tyr Thr Ile
            180                 185                 190

Asn Ile Thr Ile Lys Leu Thr Asp Lys Gly Asn Ile Gln Ile Trp Leu
        195                 200                 205

Pro Gln Phe Lys Ser Asp Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asn Asn Pro Lys Ser Asp Gly Lys Phe Tyr Leu Arg Lys Ile Asn Asp
            260                 265                 270

Asp Thr Lys Glu Ile Ala Tyr Thr Leu Ser Leu Leu Ala Gly Lys
        275                 280                 285

Ser Leu Thr Pro Thr Asn Gly Thr Ser Leu Asn Ile Ala Asp Ala Ala
    290                 295                 300

Ser Leu Glu Thr Asn Trp Asn Arg Ile Thr Ala Val Thr Met Pro Glu
305                 310                 315                 320

Ile Ser Val Pro Val Leu Cys Trp Pro Gly Arg Leu Gln Leu Asp Ala
                325                 330                 335

Lys Val Glu Asn Pro Glu Ala Gly Gln Tyr Met Gly Asn Ile Asn Val
            340                 345                 350

Thr Phe Thr Pro Ser Ser Gln Thr Leu
        355                 360
```

<210> SEQ ID NO 28
<211> LENGTH: 361
<212> TYPE: PRT
<213> ORGANISM: Escherichia coli

<400> SEQUENCE: 28

-continued

```
Met Asn Lys Ile Leu Phe Ile Phe Thr Leu Phe Phe Ser Ser Val Leu
 1               5                  10                  15

Phe Thr Phe Ala Val Ser Ala Asp Lys Ile Pro Gly Asp Glu Asn Ile
             20                  25                  30

Thr Asn Ile Phe Gly Pro Arg Asp Arg Asn Glu Ser Ser Pro Lys His
         35                  40                  45

Asn Ile Leu Asn Asp Tyr Ile Thr Ala Tyr Ser Glu Ser His Thr Leu
 50                  55                  60

Tyr Asp Arg Met Ile Phe Leu Cys Leu Ser Ser Gln Asn Thr Leu Asn
 65                  70                  75                  80

Gly Ala Cys Pro Thr Ser Glu Asn Pro Ser Ser Ser Val Ser Gly
                 85                  90                  95

Glu Thr Asn Ile Thr Leu Gln Phe Thr Glu Lys Arg Ser Leu Ile Lys
                100                 105                 110

Arg Glu Leu Gln Ile Lys Gly Tyr Lys Arg Leu Leu Phe Lys Gly Ala
            115                 120                 125

Asn Cys Pro Ser Tyr Leu Thr Leu Asn Ser Ala His Tyr Thr Cys Asn
        130                 135                 140

Arg Asn Ser Ala Ser Gly Ala Ser Leu Tyr Leu Tyr Ile Pro Ala Gly
145                 150                 155                 160

Glu Leu Lys Asn Leu Pro Phe Gly Gly Ile Trp Asp Ala Thr Leu Lys
                165                 170                 175

Leu Arg Val Lys Arg Arg Tyr Asp Gln Thr Tyr Gly Thr Tyr Thr Ile
            180                 185                 190

Asn Ile Thr Val Lys Leu Thr Asp Lys Gly Asn Ile Gln Ile Trp Leu
        195                 200                 205

Pro Gln Phe Lys Ser Asp Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Leu Arg Phe Gln Asp
                245                 250                 255

Asn Asn Pro Lys Ser Asp Gly Lys Phe Tyr Leu Arg Lys Ile Asn Asp
            260                 265                 270

Asp Thr Lys Glu Ile Ala Tyr Thr Leu Ser Leu Leu Ala Gly Lys
        275                 280                 285

Ser Leu Thr Pro Thr Asn Gly Thr Ser Leu Asn Ile Ala Asp Ala Ala
    290                 295                 300

Ser Leu Glu Ile Asn Trp Asn Arg Ile Thr Ala Val Thr Met Pro Glu
305                 310                 315                 320

Ile Ser Val Pro Val Leu Cys Trp Pro Gly Arg Leu Gln Leu Asp Ala
                325                 330                 335

Lys Val Glu Asn Pro Glu Ala Gly Gln Tyr Met Gly Asn Ile Asn Ile
            340                 345                 350

Thr Phe Thr Pro Ser Ser Gln Thr Leu
        355                 360
```

<210> SEQ ID NO 29
<211> LENGTH: 363
<212> TYPE: PRT
<213> ORGANISM: Escherichia coli

<400> SEQUENCE: 29

```
Met Lys Lys Ile Phe Ile Phe Leu Ser Ile Ile Phe Ser Ala Val Val
```

```
              1               5                  10                 15
            Ser Ala Gly Arg Tyr Pro Glu Thr Thr Val Gly Asn Leu Thr Lys Ser
                           20                 25                 30

Phe Gln Ala Pro Arg Leu Asp Arg Ser Val Gln Ser Pro Ile Tyr Asn
                           35                 40                 45

Ile Phe Thr Asn His Val Ala Gly Tyr Ser Leu Ser His Ser Leu Tyr
             50                 55                 60

Asp Arg Ile Val Phe Leu Cys Thr Ser Ser Asn Pro Val Asn Gly
             65                 70                 75                 80

Ala Cys Pro Thr Ile Gly Thr Ser Gly Val Gln Tyr Gly Thr Thr
                               85                 90                 95

Ile Thr Leu Gln Phe Thr Glu Lys Arg Ser Leu Ile Lys Arg Asn Ile
                          100                105                110

Asn Leu Ala Gly Asn Lys Lys Pro Ile Trp Glu Asn Gln Ser Cys Asp
                          115                120                125

Phe Ser Asn Leu Met Val Leu Asn Ser Lys Ser Trp Ser Cys Gly Ala
                          130                135                140

His Gly Asn Ala Asn Gly Thr Leu Leu Asn Leu Tyr Ile Pro Ala Gly
            145                150                155                160

Glu Ile Asn Lys Leu Pro Phe Gly Gly Ile Trp Glu Ala Thr Leu Ile
                          165                170                175

Leu Arg Leu Ser Arg Tyr Gly Glu Val Ser Ser Thr His Tyr Gly Asn
                          180                185                190

Tyr Thr Val Asn Ile Thr Val Asp Leu Thr Asp Lys Gly Asn Ile Gln
                          195                200                205

Val Trp Leu Pro Gly Phe His Ser Asn Pro Arg Val Asp Leu Asn Leu
                          210                215                220

Arg Pro Ile Gly Asn Tyr Lys Tyr Ser Gly Ser Asn Ser Leu Asp Met
            225                230                235                240

Cys Phe Tyr Asp Gly Tyr Ser Thr Asn Ser Asp Ser Met Val Ile Lys
                          245                250                255

Phe Gln Asp Asp Asn Pro Thr Asn Ser Ser Glu Tyr Asn Leu Tyr Lys
                          260                265                270

Ile Gly Gly Thr Glu Lys Leu Pro Tyr Ala Val Ser Leu Leu Met Gly
                          275                280                285

Glu Lys Ile Phe Tyr Pro Val Asn Gly Gln Ser Phe Thr Ile Asn Asp
                          290                295                300

Ser Ser Val Leu Glu Thr Asn Trp Asn Arg Val Thr Ala Val Ala Met
            305                310                315                320

Pro Glu Val Asn Val Pro Val Leu Cys Trp Pro Ala Arg Leu Leu Leu
                          325                330                335

Asn Ala Asp Val Asn Ala Pro Asp Ala Gly Gln Tyr Ser Gly Gln Ile
                          340                345                350

Tyr Ile Thr Phe Thr Pro Ser Val Glu Asn Leu
                          355                360

<210> SEQ ID NO 30
<211> LENGTH: 363
<212> TYPE: PRT
<213> ORGANISM: Escherichia coli

<400> SEQUENCE: 30

Met Lys Lys Ile Phe Ile Phe Leu Ser Ile Ile Phe Ser Ala Val Val
            1               5                  10                 15
```

-continued

Ser Ala Gly Arg Tyr Pro Glu Thr Thr Val Gly Asn Leu Thr Lys Ser
             20                  25                  30

Phe Gln Ala Pro Arg Leu Asp Arg Ser Val Gln Ser Pro Ile Tyr Asn
         35                  40                  45

Ile Phe Thr Asn His Val Ala Gly Tyr Ser Leu Ser His Arg Leu Tyr
    50                  55                  60

Asp Arg Ile Val Phe Val Cys Thr Ser Ser Asn Pro Val Asn Gly
65                  70                  75                  80

Ala Cys Pro Thr Ile Gly Thr Ser Gly Val Glu Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Phe Ser Asn Leu Met Val Leu Asn Ser Lys Ser Trp Ser Cys Gly Ala
    130                 135                 140

Gln Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205

Val Trp Leu Pro Gly Phe His Ser Asn Pro Arg Val Asp Leu Asn Leu
    210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Asn Ser Ser Glu Tyr Asn Leu Tyr Lys
            260                 265                 270

Arg Gly Gly Thr Glu Lys Leu Pro Tyr Ala Val Ser Leu Leu Met Gly
        275                 280                 285

Gly Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu
        355                 360

<210> SEQ ID NO 31
<211> LENGTH: 363
<212> TYPE: PRT
<213> ORGANISM: Escherichia coli

<400> SEQUENCE: 31

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
             20                  25                  30

Phe Gln Ala Pro Arg Leu Asp Arg Ser Val Gln Ser Pro Ile Tyr Asn
                35                  40                  45

Ile Phe Thr Asn His Val Ala Gly Tyr Ser Leu Ser His Arg Leu Tyr
         50                  55                  60

Asp Arg Ile Val Phe Val Cys Thr Ser Ser Asn Pro Val Asn Gly
 65                  70                  75                  80

Ala Cys Pro Thr Ile Gly Thr Ser Gly Val Glu Tyr Gly Thr Thr
                 85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
            115                 120                 125

Phe Ser Asn Leu Met Val Leu Asn Ser Lys Ser Trp Ser Cys Gly Ala
            130                 135                 140

Gln Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
            195                 200                 205

Val Trp Leu Pro Gly Phe His Ser Asn Pro Arg Val Asp Leu Asn Leu
            210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Asn Ser Ser Glu Tyr Asn Leu Tyr Lys
            260                 265                 270

Arg Gly Gly Thr Glu Lys Leu Pro Tyr Ala Val Ser Leu Leu Met Gly
            275                 280                 285

Gly Lys Ile Phe Tyr Pro Val Asn Gly Gln Ser Phe Thr Ile Asn Asp
        290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu
            355                 360

<210> SEQ ID NO 32
<211> LENGTH: 355
<212> TYPE: PRT
<213> ORGANISM: Escherichia coli

<400> SEQUENCE: 32

Met Phe Leu Cys Ser Gln Val Tyr Gly Gln Ser Trp His Thr Asn Val
1               5                   10                  15

Glu Ala Gly Ser Ile Asn Lys Thr Glu Ser Ile Gly Pro Ile Asp Arg
            20                  25                  30

Ser Ala Ala Ala Ser Tyr Pro Ala His Tyr Ile Phe His Glu His Val

-continued

```
                35                  40                  45
Ala Gly Tyr Asn Lys Asp His Ser Leu Phe Asp Arg Met Thr Phe Leu
 50                  55                  60

Cys Met Ser Ser Thr Asp Ala Ser Lys Gly Ala Cys Pro Thr Gly Glu
 65                  70                  75                  80

Asn Ser Lys Ser Ser Gln Gly Glu Thr Asn Ile Lys Leu Ile Phe Thr
                 85                  90                  95

Glu Lys Lys Ser Leu Ala Arg Lys Thr Leu Asn Leu Lys Gly Tyr Lys
                100                 105                 110

Arg Phe Leu Tyr Glu Ser Asp Arg Cys Ile His Tyr Val Asp Lys Met
                115                 120                 125

Asn Leu Asn Ser His Thr Val Lys Cys Val Gly Ser Phe Thr Arg Gly
130                 135                 140

Val Asp Phe Thr Leu Tyr Ile Pro Gln Gly Ile Asp Gly Leu Leu
145                 150                 155                 160

Thr Gly Gly Ile Trp Glu Ala Thr Leu Glu Leu Arg Val Lys Arg His
                165                 170                 175

Tyr Asp Tyr Asn His Gly Thr Tyr Lys Val Asn Ile Thr Val Asp Leu
                180                 185                 190

Thr Asp Lys Gly Asn Ile Gln Val Trp Thr Pro Lys Phe His Ser Asp
                195                 200                 205

Pro Arg Ile Asp Leu Asn Leu Arg Pro Glu Gly Asn Gly Lys Tyr Ser
210                 215                 220

Gly Ser Asn Val Leu Glu Met Cys Leu Tyr Asp Gly Tyr Ser Thr His
225                 230                 235                 240

Ser Gln Ser Ile Glu Met Arg Phe Gln Asp Asp Ser Gln Thr Gly Asn
                245                 250                 255

Asn Glu Tyr Asn Leu Ile Lys Thr Gly Glu Pro Leu Lys Lys Leu Pro
                260                 265                 270

Tyr Lys Leu Ser Leu Leu Leu Gly Gly Arg Glu Phe Tyr Pro Asn Asn
                275                 280                 285

Gly Glu Ala Phe Thr Ile Asn Asp Thr Ser Ser Leu Phe Ile Asn Trp
290                 295                 300

Asn Arg Ile Lys Ser Val Ser Leu Pro Gln Ile Ser Ile Pro Val Leu
305                 310                 315                 320

Cys Trp Pro Ala Asn Leu Thr Phe Met Ser Glu Leu Asn Asn Pro Glu
                325                 330                 335

Ala Gly Glu Tyr Ser Gly Ile Leu Asn Val Thr Phe Thr Pro Ser Ser
                340                 345                 350

Ser Ser Leu
        355

<210> SEQ ID NO 33
<211> LENGTH: 395
<212> TYPE: PRT
<213> ORGANISM: Escherichia coli

<400> SEQUENCE: 33

Met Lys Lys Val Ile Phe Val Leu Ser Met Phe Leu Cys Ser Gln Val
 1                   5                  10                  15

Tyr Gly Gln Ser Trp His Thr Asn Val Glu Ala Gly Ser Ile Asn Lys
                 20                  25                  30

Thr Glu Ser Ile Gly Pro Ile Asp Arg Ser Ala Ala Ser Tyr Pro
                 35                  40                  45
```

```
Ala His Tyr Ile Phe His Glu His Val Ala Gly Tyr Asn Lys Asp His
 50                  55                  60
Ser Leu Phe Asp Arg Met Thr Phe Leu Cys Met Ser Ser Thr Asp Ala
 65                  70                  75                  80
Ser Lys Gly Ala Cys Pro Thr Gly Glu Asn Ser Lys Ser Ser Gln Gly
                 85                  90                  95
Glu Thr Asn Ile Lys Leu Ile Phe Thr Glu Lys Lys Ser Leu Ala Arg
            100                 105                 110
Lys Thr Leu Asn Leu Lys Gly Tyr Lys Arg Phe Leu Tyr Glu Ser Asp
        115                 120                 125
Arg Cys Ile His Tyr Val Asp Lys Met Asn Leu Asn Ser His Thr Val
130                 135                 140
Lys Cys Val Gly Ser Phe Thr Arg Gly Val Asp Phe Thr Leu Tyr Ile
145                 150                 155                 160
Pro Gln Gly Glu Ile Asp Gly Leu Leu Thr Gly Ile Trp Glu Ala
                165                 170                 175
Thr Leu Glu Leu Arg Val Lys Arg His Tyr Asp Tyr Asn His Gly Thr
            180                 185                 190
Tyr Lys Val Asn Ile Thr Val Asp Leu Thr Asp Lys Gly Asn Ile Gln
        195                 200                 205
Val Trp Thr Pro Lys Phe His Ser Asp Pro Arg Ile Asp Leu Asn Leu
    210                 215                 220
Arg Pro Glu Gly Asn Gly Lys Tyr Ser Gly Ser Asn Val Leu Glu Met
225                 230                 235                 240
Cys Leu Tyr Asp Gly Tyr Ser Thr His Ser Gln Ser Ile Glu Met Arg
                245                 250                 255
Phe Gln Asp Asp Ser Gln Thr Gly Asn Asn Glu Tyr Asn Leu Ile Lys
            260                 265                 270
Thr Gly Glu Pro Leu Lys Lys Leu Pro Tyr Lys Leu Ser Leu Leu Leu
        275                 280                 285
Gly Gly Arg Glu Phe Tyr Pro Asn Asn Gly Glu Ala Phe Thr Ile Asn
    290                 295                 300
Asp Thr Ser Ser Leu Phe Ile Asn Trp Asn Arg Ile Lys Ser Val Ser
305                 310                 315                 320
Leu Pro Gln Ile Ser Ile Pro Val Leu Cys Trp Pro Ala Asn Leu Thr
                325                 330                 335
Phe Met Ser Glu Leu Asn Asn Pro Glu Ala Gly Tyr Ser Gly Ile
            340                 345                 350
Leu Asn Val Thr Phe Thr Pro Ser Ser Ser Leu Asp Asn Lys Gln
        355                 360                 365
Ala Glu Lys Asn Ile Thr Val Thr Ala Ser Val Asp Pro Thr Ile Asp
370                 375                 380
Leu Met Gln Leu Glu His His His His His
385                 390                 395

<210> SEQ ID NO 34
<211> LENGTH: 1188
<212> TYPE: DNA
<213> ORGANISM: Escherichia coli

<400> SEQUENCE: 34
atgaaaaaag tgattttgt tttatccatg tttctatgtt ctcaggttta cgggcaatca    60
tggcatacga acgtagaggc tggttcaata aataaaacag agtcgatagg ccccatagac   120
cgaagtgctg ctgcatcgta tcctgctcat atatatttc atgaacatgt tgctggttac   180
```

```
aataaagatc actctctttt tgacaggatg acgtttttat gtatgtcatc aacagatgca    240
tctaaaggtg catgtccgac aggagaaaac tccaaatcct ctcaagggga gactaatatt    300
aagctaatat ttactgaaaa gaaaagtctg gccagaaaaa cattaaactt aaaaggatat    360
aagagatttt tatatgaatc agatagatgc attcattatg tcgataaaat gaatctcaat    420
tctcatactg ttaaatgtgt aggttcattc acaagaggag tagatttcac tttatatatc    480
ccacaaggtg aaattgatgg gcttctaact ggaggtatat gggaggcaac actagagtta    540
cgagtcaaaa ggcattacga ctataatcat ggtacttaca agttaatat cacagttgat     600 ttgacagaca aaggaaatat tcaggtctgg acaccaaagt ttcatagcga tcctagaatt    660
gatctgaatt tacgtcctga aggtaatggt aaatattctg gtagtaacgt gcttgagatg    720
tgtctctatg atggctatag tacacatagt caaagtatag aaatgaggtt tcaggatgac    780
tcacaaacag gaaataatga atataatctt ataaaaactg gagagccatt aaaaaaattg    840
ccatataaac tttctcttct tttaggagga cgagagtttt atccaaataa tggagaggct    900
tttactatta atgatacttc gtcattgttt ataaactgga atcgtattaa gtctgtatcc    960
ttaccacaga ttagtattcc agtactatgc tggccagcaa acttgacatt tatgtcagag   1020
ctaaataatc cagaagcggg tgagtattca ggaatactta acgtaacatt tactcctagt   1080
agttcaagtc tggacaataa acaagccgag aaaaatatca ctgtaactgc tagcgttgat   1140
ccaactatcg atctgatgca actcgagcac caccaccacc accactga                1188
```

<210> SEQ ID NO 35
<211> LENGTH: 210
<212> TYPE: PRT
<213> ORGANISM: Escherichia coli

<400> SEQUENCE: 35

```
Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Tyr Thr Ile
            180                 185                 190
```

```
Asn Ile Thr Val Asn Leu Thr Asp Lys Gly Leu Glu His His His
        195                 200                 205

His His
    210

<210> SEQ ID NO 36
<211> LENGTH: 213
<212> TYPE: PRT
<213> ORGANISM: Escherichia coli

<400> SEQUENCE: 36

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Gln Asp Arg Ser Val Gln Ser Pro Ile Tyr Asn
        35                  40                  45

Ile Phe Thr Asn His Val Ala Gly Tyr Ser Leu Ser His Asn Leu Tyr
    50                  55                  60

Asp Arg Ile Val Phe Leu Cys Thr Ser Ser Asn Pro Val Asn Gly
65                  70                  75                  80

Ala Cys Pro Thr Leu Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Thr Ser Asn Leu Met Val Leu Asn Ser Lys Ser Trp Ser Cys Gly His
    130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Leu Glu His
        195                 200                 205

His His His His His
    210

<210> SEQ ID NO 37
<211> LENGTH: 213
<212> TYPE: PRT
<213> ORGANISM: Escherichia coli

<400> SEQUENCE: 37

Met Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
            20                  25                  30

Thr Glu Ser Ile Gly Pro Ile Asp Arg Ser Ala Ala Ser Tyr Pro
        35                  40                  45

Ala His Tyr Ile Phe His Glu His Val Ala Gly Tyr Asn Lys Asp His
    50                  55                  60

Ser Leu Phe Asp Arg Met Thr Phe Leu Cys Met Ser Ser Thr Asp Ala
65                  70                  75                  80
```

-continued

```
Ser Lys Gly Ala Cys Pro Thr Gly Glu Asn Ser Lys Ser Ser Gln Gly
                85              90              95

Glu Thr Asn Ile Lys Leu Ile Phe Thr Glu Lys Lys Ser Leu Ala Arg
            100             105             110

Lys Thr Leu Asn Leu Lys Gly Tyr Lys Arg Phe Leu Tyr Glu Ser Asp
        115             120             125

Arg Cys Ile His Tyr Val Asp Lys Met Asn Leu Asn Ser His Thr Val
    130             135             140

Lys Cys Val Gly Ser Phe Thr Arg Gly Val Asp Phe Thr Leu Tyr Ile
145             150             155                     160

Pro Gln Gly Glu Ile Asp Gly Leu Leu Thr Gly Gly Ile Trp Glu Ala
                165             170             175

Thr Leu Glu Leu Arg Val Lys Arg His Tyr Asp Tyr Asn His Gly Thr
            180             185             190

Tyr Lys Val Asn Ile Thr Val Asp Leu Thr Asp Lys Gly Leu Glu His
        195             200             205

His His His His His
        210
```

ANTI-ADHESIN BASED PASSIVE IMMUNOPROPHYLACTIC

CROSS-REFERENCE TO RELATED APPLICATIONS

This application claims priority to U.S. Provisional Application 60/683,787 filed May 24, 2005, and is the divisional application of U.S. application Ser. No. 11/439,061 filed May 23, 2006 (now abandoned).

FIELD OF INVENTION

This inventive subject matter relates to a pharmaceutical useful in conferring passive protection against diarrhea caused by enterotoxigenic *Escherichia coli*.

SEQUENCE LISTING

I hereby state that the information recorded in computer readable form is identical to the written sequence listing.

BACKGROUND OF INVENTION

Enterotoxigenic *Escherichia coli* (ETEC) are a principal cause of diarrhea in young children in resource-limited countries and also travelers to these areas (1, 2). ETEC produce disease by adherence to small intestinal epithelial cells and expression of a heat-labile (LT) and/or heat-stable (ST) enterotoxin (3). ETEC typically attach to host cells via filamentous bacterial surface structures known as colonization factors (CFs). More than 20 different CFs have been described, a minority of which have been unequivocally incriminated in pathogenesis (4).

Firm evidence for a pathogenic role exists for colonization factor antigen I (CFA/I), the first human-specific ETEC CF to be described. CFA/I is the archetype of a family of eight ETEC fimbriae that share genetic and biochemical features (5, 4, 6, 7). This family includes *coli* surface antigen 1 (CS1), CS2, CS4, CS14, CS17, CS19 and putative colonization factor O71 (PCFO71). The complete DNA sequences of the gene clusters encoding CFA/I, CS1 and CS2 have been published (8, 9, 10, 11, 12). The genes for the major subunit of two of the other related fimbriae have been reported (13, 6). The four-gene bioassembly operons of CFA/I, CS1, and CS2 are similarly organized, encoding (in order) a periplasmic chaperone, major fimbrial subunit, outer membrane usher protein, and minor fimbrial subunit. CFA/I assembly takes place through the alternate chaperone pathway, distinct from the classic chaperone-usher pathway of type I fimbrial formation and that of other filamentous structures such as type IV pili (14, 15). Based on the primary sequence of the major fimbrial subunit, CFA/I and related fimbriae have been grouped as class 5 fimbriae (16).

Studies of CS1 have yielded details on the composition and functional features of Class 5 fimbriae (17). The CS1 fimbrial stalk consists of repeating CooA major subunits. The CooD minor subunit is allegedly localized to the fimbrial tip, comprises an extremely small proportion of the fimbrial mass, and is required for initiation of fimbrial formation (18). Contrary to earlier evidence suggesting that the major subunit mediates binding (19), recent findings have implicated the minor subunit as the adhesin and identified specific amino acid residues required for in vitro adhesion of CS1 and CFA/I fimbriae (20). The inferred primary amino acid structure of those major subunits that have been sequenced share extensive similarity. Serologic cross-reactivity of native fimbriae is, however, limited, and the pattern of cross-reactivity correlates with phylogenetically defined subtaxons of the major subunits (13).

Implication of the minor subunits of Class 5 fimbriae as the actual adhesins entreats scrutiny regarding the degree of their conservation relative to that of the major subunits. It was speculated that CooD and its homologs retained greater similarity due to functional constraints imposed by ligand binding requirements and/or its immunorecessiveness, itself attributable to the extremely large ratio of major to minor subunits in terms of fimbrial composition. Studies were conducted to examine the evolutionary relationships of the minor and major subunits of Class 5 ETEC fimbriae as well as the two assembly proteins (21). It was demonstrated that evolutionary distinctions exist between the Class 5 major and minor fimbrial subunits and that the minor subunits function as adhesins. These findings provide practical implications for vaccine-related research.

The nucleotide sequence of the gene clusters that encode CS4, CS14, CS17, CS19 and PCFO71 was determined from wild type diarrhea-associated isolates of ETEC that tested positive for each respective fimbria by monoclonal antibody-based detection (21). The major subunit alleles of the newly sequenced CS4, CS14, CS17 and CS19 gene clusters each showed 99-100% nucleotide sequence identity with corresponding gene sequence(s) previously deposited in GenBank, with no more than four nucleotide differences per allele. Each locus had four open reading frames that encoded proteins with homology to the CFA/I class chaperones, major subunits, ushers and minor subunits. As previously reported (13), the one exception was for the CS14 gene cluster, which contained two tandem open reading frames downstream of the chaperone gene. Their predicted protein sequences share 94% amino acid identity with one another and are both homologous to other Class 5 fimbriae major subunits.

Examination of the inferred amino acid sequences of all the protein homologs involved in Class 5 fimbrial biogenesis reveals many basic similarities. Across genera, each set of homologs generally share similar physicochemical properties in terms of polypeptide length, mass, and theoretical isoelectric point. All of the involved proteins contain an amino-terminal signal peptide that facilitates translocation to the periplasm via the type II secretion pathway. None of the major subunit proteins contain any cysteine residues, while the number and location of six cysteine residues are conserved for all of the minor subunits except that of the *Y. pestis* homolog 3802, which contains only four of these six residues.

Type 1 and P fimbriae have been useful models in elucidating the genetic and structural details of fimbriae assembled by the classical chaperone-usher pathway (23, 24, 25). An outcome of this work has been development of the principle of donor strand complementation, a process in which fimbrial subunits non-covalently interlock with adjoining subunits by iterative intersubunit sharing of a critical, missing β-strand (22, 26). Evidence has implicated this same mechanism in the folding and quaternary conformational integrity of *Haemophilus influenzae* hemagglutinating pili (28), and *Yersinia pestis* capsular protein, a non-fimbrial protein polymer (29). Both of these structures are distant Class I relatives of Type 1 and P fimbriae that are assembled by the classical chaperone-usher pathway. From an evolutionary perspective, this suggests that the mechanism of donor strand complementation arose in a primordial fimbrial system from which existing fimbriae of this Class have derived. While donor strand complementation represents a clever biologic solution to the problem of protein folding for noncovalently linked, polymeric surface proteins, its exploitation by adhesive fimbriae other than those of the classical usher-chaperone pathway has not been demonstrated.

Common to fimbriae assembled by the alternate chaperone pathway and the classical chaperone-usher pathway are the requirement for a periplasmic chaperone to preclude subunit misfolding and an usher protein that choreographs polymerization at the outer membrane. That the fimbrial assembly and structural components of these distinct pathways share no sequence similarity indicates that they have arisen through convergent evolutionary paths. Nevertheless, computational analyses of the CFA/I structural subunits suggests the possibility that donor strand complementation may also govern chaperone-subunit and subunit-subunit interaction.

The eight ETEC Class 5 fimbriae clustered into three subclasses of three (CFA/I, CS4, and CS14), four (CS1, PCFO71, CS17 and CS19), and one (CS2) member(s) (referred to as subclasses 5a, 5b, and 5c, respectively) (21). Previous reports demonstrated that ETEC bearing CFA/I, CS2, CS4, CS14 and CS19 manifest adherence to cultured Caco-2 cells (6, 22). However, conflicting data have been published regarding which of the component subunits of CFA/I and CS1 mediate adherence (19, 20).

This question of which fimbrial components is responsible for mediating adherence was approached by assessing the adherence-inhibition activity of antibodies to intact CFA/I fimbriae, CfaB (major subunit), and to non-overlapping amino-terminal (residues 23-211) and carboxy-terminal (residues 212-360) halves of CfaE (minor subunit) in two different in vitro adherence models (21). It was demonstrated that the most important domain for CFA/I adherence resides in the amino-terminal half of the adhesin CfaE (21).

The studies briefly described above provide evidence that the minor subunits of CFA/I and other Class 5 fimbriae are the receptor binding moiety (20, 21). Consistent with these observations, because of the low levels of sequence divergence of the minor subunits observed within fimbrial subclasses 5a and 5b (20), the evolutionary relationships correlated with cross-reactivity of antibodies against the amino-terminal half of minor subunits representing each of these two subclasses (21). These studies strongly suggest that the minor subunits of class 5 fimbriae are much more effective in inducing antiadhesive immunity and thus an important immunogen for inducing protective antibody (21).

Anti-diarrheal vaccines would be a preferable method of conferring protection against diarrheal disease including ETEC caused diarrhea. However, because of the complexities of constructing and licensing of effective vaccines other methods to confer interim protection have been sought. A measure shown to hold considerable promise in the prevention of diarrhea is passive, oral administration of immunoglobulins against diarrhea causing enteropathogens. Products with activity against ETEC, *Shigella*, and rotavirus have been shown to prevent diarrhea in controlled studies with anti-cryptosporidial bovine milk immunoglobulins (BIgG) preparations (30-33). Furthermore, favorable encouraging results have been observed using this approach with anti-cryptosporidial BIgG preparations (34, 35).

Accordingly, an object of this invention is an immunoglobulin supplement capable of providing prophylactic protection against ETEC infection. Because the minor subunit (adhesin) is the fimbrial component directly responsible for adherence, administration of anti-adhesin antibodies will likely confer significantly greater protection than antibodies raised against intact fimbriae or intact bacteria. Furthermore, another object of the invention is a method for the production of passive prophylactic formulation against ETEC, containing anti-adhesin immunoglobulin. The use of recombinant minor fimbrial subunit polypeptides in the immunoglobulin production method will provide enhanced antibody yields and standardization over the use of intact fimbriae or whole cells.

SUMMARY OF INVENTION

Vaccines are the preferred method for conferring anti-diarrhea protection in potentially exposed populations. However, there are no currently licensed effective vaccines against ETEC. Therefore, an interim protective measure, until vaccines can be developed, is the administration of oral passive protection in the form of anti-adhesin immunoglobulin supplements derived from bovine, or other milk producing animal, colostrum or milk.

An object of the invention is a anti-*Escherichia coli* antibody prophylactic formulation that is specific to class 5 enterotoxigenic *E. coli* fimbriae adhesin.

Another object of the invention is a method for conferring passive immunity using an anti-*E. coli* antibody prophylactic formulation that is specific to class five *Escherichia coli* fimbriae adhesin including CfaE and CsbD.

An additional object of the invention is a method of conferring passive immunity to enterotoxigenic *E. coli* by administering a food supplement containing anti-*E. coli* antibody specific to Class 5 fimbriae adhesins.

A still further object of the invention is a method of producing an anti-*E. coli* adhesin milk antibody by administering recombinant adhesin polypeptides to domestic animals such as cows.

BRIEF DESCRIPTION OF THE DRAWINGS

FIG. 1. A highly conserved β-strand motif in the major structural subunits of Class 5 fimbriae. This is a multiple alignment of the amino-termini of the mature form of the major subunits, with consensus sequence shown below. This span is predicted to form an interrupted β-strand motif spanning residues 5-19 (demarcated by yellow arrows below consensus). Shading of conserved residues indicates class as follows: blue, hydrophobic; red, negatively charged residues; turquoise, positively charged residues; and green, proline. Also shown are the sequence identification numbers (SEQ ID No.) for the associated polypeptides. Abbrevations: Bcep, *Burkholderia cepacia*; Styp, *Salmonella typhi*. U, hydrophobic residue; x, any residue; Z, E or Q.

DETAILED DESCRIPTION AND PREFERRED EMBODIMENTS

Figure 2:
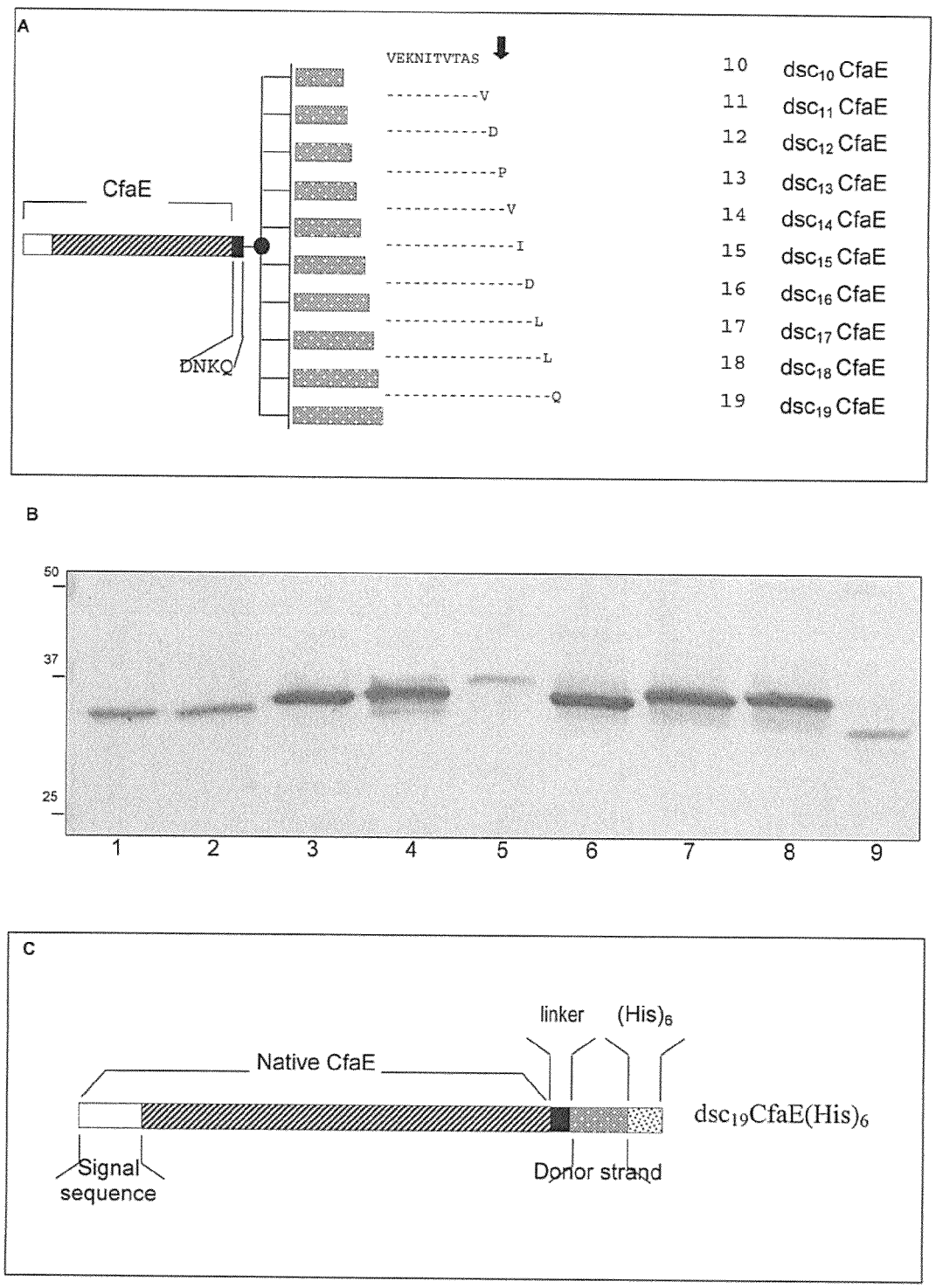
FIG. 2. Panel A, Schematic diagram showing the domains of independent CfaE variant constructs with C-terminal extensions comprising the N-terminal β-strand span of CfaB varying in length from 10 to 19 residues. Each construct contains a short flexible linker peptide (DNKQ) intercalated between the C-terminus of the native CfaE sequence and the donor β-strand. The vertical arrow identifies the donor strand valine that was modified to either a proline (V7P) to disrupt the secondary β-strand motif. Panel B, Western blot analysis of periplasmic concentrates from the series of strains engineered to express CfaE and the variants complemented in cis with varying lengths of the amino-terminal span of mature CfaB. The primary antibody preparations used were polyclonal rabbit antibody against CfaE. Lanes correspond to preparations from the following constructs: Lane 1, dsc10CfaE; 2, dsc11CfaE; 3, dsc12CfaE; 4, dsc13CfaE; 5, dsc13CfaE[V7P]; 6, dsc14CfaE; 7, dsc16CfaE; 8, dsc19CfaE; and 9, CfaE. Molecular weight markers (in kD) are shown to the left. Panel C, schematic representation of the engineered components of dsc19CfaE(His)6, containing the native CfaE sequence (including its Sec-dependent N-terminal signal sequence), with an extension at its C-terminus consisting of a short linker sequence (i.e., DNKQ), the 19 residue donor strand from the N-terminus of mature CfaB, and a terminal hexahistidine affinity tag.

Vaccines are the preferred prophylactic measure for long-term protection against ETEC caused diarrhea. However, development of effective vaccines is typically difficult and time-intensive. Furthermore, even after an effective ETEC vaccine is developed, protection against ETEC caused disease is not conferred until an adequate dose regimen is completed. Therefore, there is a need for effective, safe and easy to take passive prophylactic measures. A particularly promising approach, for example, is the use of bovine milk immunoglobulins (BIgG) preparations (30-33).

Computational analyses of the CFA/I structural subunits suggest that donor strand complementation governs chaperone-subunit and subunit-subunit interaction. The major subunits of Class 5 fimbriae share a highly conserved amino-terminal span predicted to form a β strand (FIG. 1). Based on its predicted structure and location, the β-strand-like structure is donated to neighboring major subunit (e.g. CfaB) along the alpha-helical stalk and to an adhesin (e.g. CfaE) at the fimbrial tip. The highly conserved nature of the amino-terminal β strand of CfaB and its homologs, together with the precedent that the amino-terminus of type 1 fimbrial subunits functions as the exchanged donor strand in filament assembly suggested this as a good candidate for the donor β strand that noncovalently interlocks CFA/I subunits.

ETEC fimbriae are classified based on genetic and structural analysis and many fimbriae associated with disease fall into the Class 5 fimbrial grouping, which includes CFA/I, CS17 and CS2. Class 5 fimbriae adhesins each share significant characteristics that clearly differentiate these members as belonging to a recognizable genus. Although Class 5 fimbriae are distinguishable serologically, they share similar architecture in that they are composed of a major stalk forming subunit (e.g., CfaB of CFA/I) and a minor tip-localized subunit (e.g., CfaE of CFA/I) that we have found serves as the intestinal adhesin. A comparison of amino acid sequences of the major and minor subunits (i.e., fimbrial adhesins) clearly show a strong amino acid sequence relatedness as well as sequence homology, as illustrated in Table 1, for the major subunits and Table 2 for adhesin molecules. In Table 1 and 2 the shaded areas show similarity of residues and the unshaded areas show residue identity. As illustrated in Table 2, the fimbrial adhesins display, as well as the major subunits, a high level of residue identity, ranging from 47% to 98%. Additionally, fimbrial adhesins have significant amino acid sequence conservation, including a conserved structural motif in the carboxy-terminal domain of both the major and minor subunits (i.e., the beta-zipper motif). This structure indicates that the C-terminal domain of these proteins are involved in subunit-subunit interaction.

TABLE 1

|      | CfaB | CooA | CotA | CsfA | CsuA$_1$ | CsbA | CsdA | CosA |
|------|------|------|------|------|----------|------|------|------|
| CfaB | —    | .53  | .51  | .66  | .58      | .50  | .52  | .52  |
| CooA | .74  | —    | .50  | .57  | .51      | .61  | .59  | .90  |
| CotA | .67  | .71  | —    | .50  | .52      | .45  | .47  | .52  |
| CsfA | .81  | .75  | .71  | —    | .62      | .54  | .55  | .56  |
| CsuA$_1$ | .75 | .72 | .71 | .78 | —       | .51  | .50  | .52  |
| CsbA | .73  | .76  | .67  | .72  | .73      | —    | .88  | .61  |
| CsdA | .72  | .75  | .69  | .71  | .72      | .92  | —    | .57  |
| CosA | .71  | .95  | .74  | .73  | .73      | .79  | .78  | —    |

3 letter codes: CFA/I, Cfa; CS1, Coo; CS2, Cot; CS4, Csf; CS14, Csu; CS17, Csb; CS19, Csd; PCFO71, Cos.

TABLE 2

|      | CfaE | CooD | CotD | CsfD | CsuD | CsbD | CsdD | CosD |
|------|------|------|------|------|------|------|------|------|
| CfaE | —    | .51  | .46  | .80  | .82  | .51  | .51  | .50  |
| CooD | .65  | —    | .49  | .51  | .50  | .97  | .97  | .98  |
| CotD | .64  | .63  | —    | .47  | .48  | .48  | .48  | .48  |
| CsfD | .87  | .65  | .64  | —    | .94  | .50  | .50  | .50  |
| CsuD | .88  | .64  | .65  | .97  | —    | .50  | .50  | .50  |
| CsbD | .66  | .97  | .62  | .65  | .65  | —    | .97  | .96  |
| CsdD | .66  | .97  | .63  | .64  | .65  | .97  | —    | .98  |
| CosD | .65  | .99  | .62  | .64  | .65  | .96  | .97  | —    |

3 letter codes: CFA/I, Cfa; CS1, Coo; CS2, Cot; CS4, Csf; CS14, Csu; CS17, Csb; CS19, Csd; PCFO71, Cos.

Toward the development of an ETEC antigen, we constructed a conformationally-stable construct wherein an amino-terminal donor β-strand of CfaB provides an in cis carboxy-terminal extension of CfaE to confer conformational stability and protease resistance to this molecule, forming a soluble monomer capable of binding human erythrocytes. In order to identify common structural motifs, multiple alignments of the amino acid sequences of the eight homologs of the major and minor subunits of Class 5 ETEC fimbriae were generated. Secondary structure prediction algorithms indicated that both subunits form an amphipathic structure rich in β-strands distributed along their length. Twenty six percent of the consensus minor subunit sequence is predicted to fold into a β-conformation, comprising 17 interspersed β strands, which might be expected to form a hydrophobic core. Sakellaris et al have previously suggested that an amino acid span forms a β-zipper motif, analogous to that of class I fimbrial subunits, that plays a role in fimbrial subunit-chaperone interaction (27).

The following example discloses the production of a CfaE immunogen using a donor strand from CfaB. However, one of skill in the art, following this disclosure, would be able to engineer constructs to serve as an immunogen using donor strands from other class 5 major subunits in conjunction with other adhesin constructs, such as CsbD, CsfD, CsuD, CooD, CosD, CsdD, and CotD. The major Class 5 fimbrial subunits are listed in Table 3 along with the corresponding SEQ ID No. corresponding to the subunit's amino acid sequence donor strand. Table 4 lists the amino acid sequence of the Class 5 adhesin and their respective SEQ ID No.

TABLE 3

| Major Subunit | SEQ ID No. of Donor Strand Amino Acid Sequence |
|---------------|------------------------------------------------|
| CfaB          | 1                                              |
| CsfA          | 2                                              |
| CsuA1         | 3                                              |
| CsuA2         | 4                                              |
| CooA          | 5                                              |

TABLE 3-continued

| Major Subunit | SEQ ID No. of Donor Strand Amino Acid Sequence |
|---|---|
| CosA | 6 |
| CsbA | 7 |
| CsdA | 8 |
| CotB | 9 |

TABLE 4

| Minor Subunit | SEQ ID. No. of Amino Acid Sequence |
|---|---|
| CfaE | 11 |
| CsbD | 22 |
| CsfD | 27 |
| CsuD | 28 |
| CooD | 29 |
| CosD | 30 |
| CsdD | 31 |
| CotD | 32 |

An inventive aspect of this invention is a method for the production of a passive prophylactic against Class 5 fimbrial adhesin of ETEC bacteria. Examples using specific Class 5 fimbrial adhesins are provided in order to illustrate the invention. However, other Class 5 fimbrial adhesins, and their associated major subunits can also be utilized by one of skill in the art Example 1

Production of Anti-CfaE Bovine Immunoglobulin

As mentioned above, the highly conserved nature of the amino-terminal β strand of CfaB and its homologs, together with other structure/function studies in type 1 fimbrial subunits, suggested this structure as a good candidate for the donor β strand that interlocks CFA/I subunits. In order to test this hypothesis with respect to the minor adhesive subunit, a plasmid was engineered to express a CfaE variant containing a C-terminal extension consisting of a flexible hairpin linker (DNKQ, SEQ ID No. 10) followed by an amino acid sequence of CfaB (FIG. 2). It was found that a CfaB donor strand length of at least 12 to as many as 19 amino acids was necessary to obtain a measurable recovery of CfaE. In studies using constructs containing a 12 to 19 amino acid donor strand, where mutations were introduced to break the β strand, it was demonstrated that the β strand is important to the observed stability achieved by the C-terminal amino acid extension. It was further determined that the C-terminal β strand contributed by CfaB in cis precludes chaperone (e.g. CfaA)-adhesin complex formation.

In this example, a recombinant CfaE antigen was constructed, as shown in FIG. 2C, by fusing a Cfa E polypeptide sequence (SEQ ID No. 11), encoded by the nucleotide sequence of SEQ ID No. 18 to the N-terminal amino acid sequence of a linker polypeptide (SEQ ID No. 10) which is in-turn linked at its C-terminus to a 19 amino acid CfaB donor strand corresponding to amino acids 1-19 of SEQ ID No. 1. Although, SEQ ID No. 10 was utilized for a linker, other amino acid sequences have been found acceptable, including SEQ ID No. 12 and 13. For this example, the CfaB major subunit donor strand used is shown in SEQ ID No. 1 which is encoded by the nucleotide sequence of SEQ ID No. 20. However, based on the observation that the a donor strand of 12 to 19 amino acids is suitable for significant CfaE recovery, a recombinant antigen containing 12 to 19 amino acids can be utilized. Similarly, recombinant peptides can be constructed containing all or a portion of SEQ ID No. 11 as long as amino acid sequence contains anti-CfaE B-cell epitopes.

The CfaE construct containing the 19 amino acid major subunit donor strand was constructed by first inserting cfaE into plasmid vectors by in vitro recombination using the GATEWAY® system (Invitrogen, Carlsbad, Calif.). Primers with the following sequences were used for the initial cloning into pDONR207™: dsc-CfaE 13-1 (forward), 5'-TCG ACA ATA AAC AAG TAG AGA AAA ATA TTA CTG TAA CAG CTA GTG TTG ATC CTT AGC-3' (SEQ ID No. 14); and dsc-CfaE 13-2 (reverse), 5'-TCG AGC TAA GGA TCA ACA CTA GCT GTT ACA GTA ATA TTT TTC TCT ACT TGT TTA TTG-3' (SEQ ID No 15). The PCR products flanked by attB recombination sites were cloned into the donor vector PDONR201™ (GATEWAY® Technology, Invitrogen, Carlsbad, Calif.), using the GATEWAY BP® reaction to generate the entry vector pRA13.3. In the GATEWAY LR® reaction the gene sequence was further subcloned from pRA13.3 into the modified expression vector pDEST14-Kn$^r$ (vector for native expression from a T7 promoter) to generate the plasmid pRA14.2. The pDEST14-Kn$^r$ vector was constructed by modifying PDEST14® (GATEWAY® Technology, Invitrogen, Carlsbad, Calif.) by replacement of ampicillin with kanamycin resistance. The presence of the correct cfaE was confirmed by sequence analysis. *E. coli* strain BL21SI™ (Invitrogen, Carlsbad, Calif.) was used for the expression of the pRA14.1 and related CfaE donor strand complemented constructs.

The above procedure was utilized to construct a CfaE/donor strand recombinant construct. However, constructs containing other adhesin molecules can also be constructed, including the minor subunits: CsfD, CsuD, CooD, CosD, CsdD, CsbD and CotD, in conjunction with the appropriate donor strand from the major subunits as listed in Table 1. For example, a recombinant CsbD construct was designed comprising a CsbD polypeptide sequence comprising all or a portion of SEQ ID No. 22 fused at the C-terminal end, via a linker polypeptide of SEQ ID No 10, to a CsbA major subunit donor strand of a polypeptide sequence SEQ ID No. 6 that is encoded by the nucleotide sequence of SEQ ID No. 21.

Development of pET/Adhesin Construct for Large Scale Antigen Production

The DNA construct encoding dsc$_{19}$CfaE was then excised from PDEST14® vector and inserted into PET24(A)™ in order to encode a variant CfaE construct that incorporates a carboxy-terminal polyhistine tail after the CfaB donor strand. This construct, with a polypeptide sequence of SEQ ID No 23 is designated dsc$_{19}$CfaE(His)$_6$ and is encoded by the nucleotide sequence of SEQ ID No. 24.

Construction of the dsc$_{19}$cfaE insert was carried out by amplifying the pDEST 14 vector by polymerase chain reaction using a NdeI containing forward primer and an XhoI containing reverse primer, SEQ ID No 16 and 17, respectively. The dsc$_{19}$cfaE coding region was directionally ligated into an NdeI/XhoI restricted pET24a plasmid. The insert containing PET24A™ plasmid was used to transform NOVABLUE-3™ BL21 (EMD Biosciences, NOVAGEN® Brand, Madison, Wis.) bacteria. Transformed colonies were then selected and re-cultured in order to expand the plasmid containing bacteria. Plasmid inserts from selected colonies were then sequenced. These plasmids were then re-inserted into BL 21 (DE3) (EMD Biosciences, NOVAGEN® Brand, Madison, Wis.) competent cells and the DNA insert sequence confirmed.

Similar to the method used to construct $dsc_{19}CfaE(His)_6$, a DNA construct encoding $dsc_{19}CsbD$ was also made by insertion of CsbD and a CsbA donor strain sequence into PET24A™. This construct has a polypeptide sequence of SEQ ID No. 25 and is encoded by the nucleotide sequence of SEQ ID No. 26. The donor strand sequence from CsbA used in designing the construct is disclosed as SEQ ID No. 6. Like the CfaE construct, the 19 amino acid sequence from CsbA corresponding to amino acids 1-19 of SEQ ID No. 6 was used. However donor strand sequences ranging from the 12 to 19 amino acids can be used.

Production of $dsc_{19}CfaE(His)_6$.

A number of growth conditions and media can be utilized for large-scale production of the $dsc_{19}CfaE(His)_6$, or other adhesin/donor strand construct. For example initiation of culture can be conducted using 1.0 μM to 1.0 mM isopropyl-β-D-thiogalactopyranosid (IPTG) at an induction temperature of 32° C. to 25° C. for 1 to 4 hours. In this example, LB media was utilized with a 1.0 μM IPTG concentration at 32° C. for 3 hours. However, APS™ and other media formulations can also be used. The $dsc_{19}CfaE(His)_6$, or other recombinant adhesin construct, is purified on a Ni column. Yield of construct is at least 0.45 to 0.9 mg of protein/L of culture.

Manufacture of BIgG

Figure 3A:
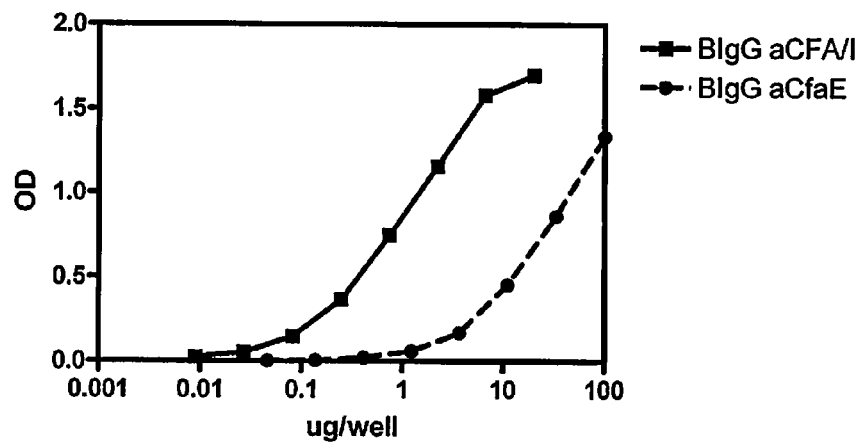
FIG. 3. Reactivity of products with a panel of CFA/I-related antigens by ELISA.
Figure 3B:
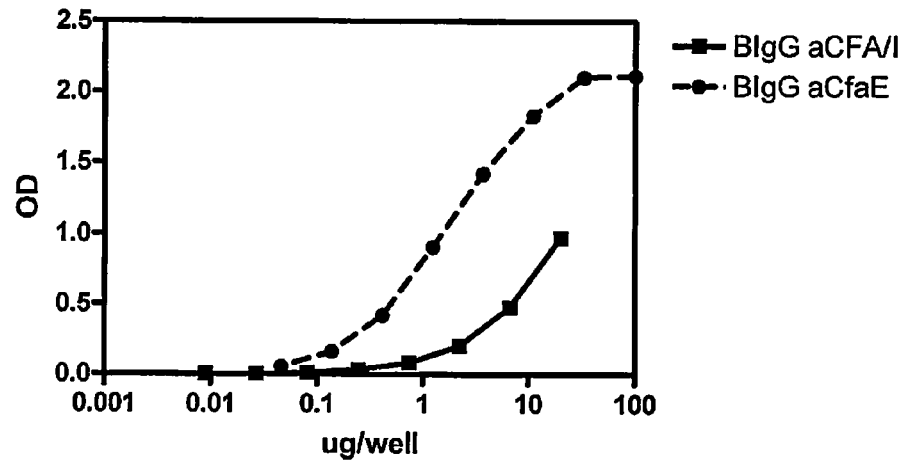

Antibody to recombinant antigen is produced in the colostrum or milk of domesticated cattle, including Holsteins. A total of three intramuscular vaccinations each in a volume of two ml containing 500 μg of antigen each is administered at a single site. Vaccinations are given approximately three weeks apart with the final vaccination 1 to 2 weeks prior to calving. At calving the first four milkings are collected, the volume estimated and a sample tested for anti-adhesin antibody by enzyme-linked immunosorbent assay (ELISA). FIG. 3 shows the reactivity of anti-CFA/I BIgG and anti-CfaE BIgG products. CFA/I BIgG gives a higher level of reactivity to CFA/I antigen than anti-CfaE by ELISA (FIG. 3A). This is due to the fact that CFA/I antigen used to coat the ELISA plate is made of primarily the CfaB major subunit and the CfaE minor subunit is present as a minor component only. As expected, the anti-CfaE BIgG product has a much stronger reaction with CfaE compared to either AEMI or anti-CFA/I BIgG (FIG. 3B). This confirms that immunization of cows with the CfaE antigen greatly enhances the generation of antibodies to adhesin, CfaE.

Further processing of the collected product can be undertaken. For example, frozen milk is fractionated to remove caseins through a cheese-making step. The whey fraction, containing most immunoglobulins is then drained from the cheese curd and pasteurized under standard dairy conditions. The immunoglobulin-enriched whey fraction is then concentrated and residual milk fat is removed by centrifugation at room temperature. Subsequently, phospholipid and non-immunoglobulin proteins can be removed (36). The final product is then concentrated to 15-20% solids and salts removed by continuous diafiltration against three buffer changes. The final product is then tested for by ELISA.

In addition to the characterization of antibody reactivity of BIgG to ETEC antigens, the functional activity of the antibodies was evaluated. As the receptor(s) for CFA/I is not defined, a surrogate assay for adhesion of ETEC to target cells in vitro was used. ETEC expressing certain fimbriae (including CFA/I) adhere to and agglutinate human and/or bovine erythrocytes in a mannose-resistant hemagglutination assay (MRHA). This is used as a surrogate marker for adhesion of ETEC whole cells, fimbriae or purified minor subunits of fimbriae to target eukaryotic epithelial cells. This phenomenon, described as hemagglutination inhibition (HAI), is an indicator of antibodies capable of neutralizing adhesion of ETEC to target cells.

Figure 4:
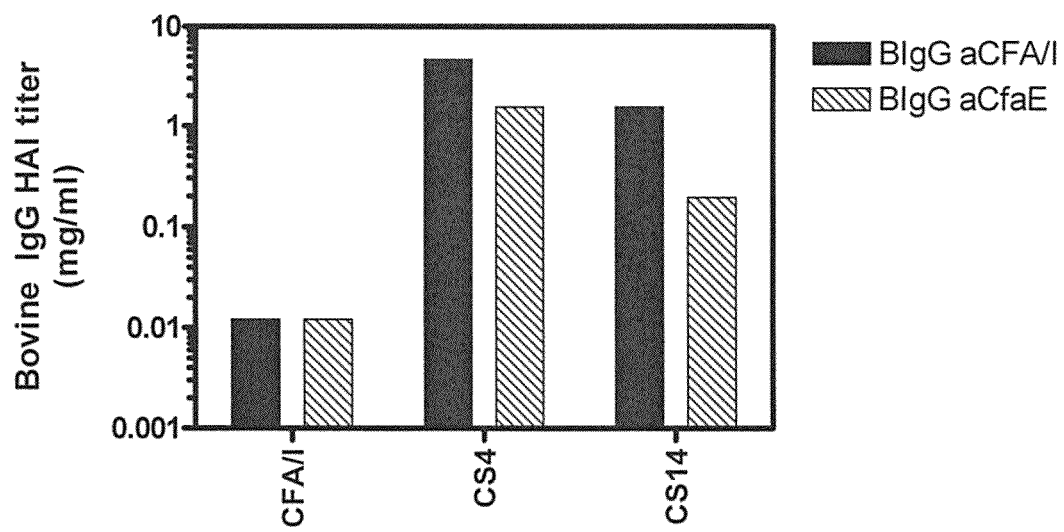
FIG. 4. In vitro functional activity of antibodies to BIgG anti-CfaE.

In FIG. 4, human erythrocytes were agglutinated by ETEC expressing CFA/I, CS4 or CS14 in a mannose-resistant manner (MRHA). This MRHA can be inhibited by pre-incubation of bacteria with anti-CFA/I BIgG or anti-CfaE BIgG. Shown in FIG. 4, both anti-CFA/I BIgG and anti-CfaE BIgG contained antibodies capable of inhibiting the ability of ETEC that express the homologous fimbriae from agglutinating human erythrocytes. FIG. 4 shows the titer of BIgG (expressed as mg IgG/ml) required to neutralized aggluntination of bovine erythrocytes by ETEC expressing different colonization factors. The concentrations of BIgG products tested were adjusted so the minimal concentrations of IgG were equal in both products. Therefore, the data is expressed as the concentration of IgG that is required to inhibit MRHA by ETEC expressing CFA/I, CS4 or CS14 fimbriae. As little as 14 to 17 μg/ml of bovine IgG present in the BIgG powders are required in vitro to inhibit MRHA.

Strong inhibitory activity is provided by anti-CFA/I, as expected, with an equivalent level of inhibition provide by anti-CfaE. Of importance is that both anti-CFA/I and anti-CfaE show cross-reactivity of binding inhibition against CS4 and CS14. This illustrates that an anti-CfaE prophylactic antibody will have utility in conferring protection against other related antigens.

Example 2

Production of Anti-CfaD (CS17) Bovine Immunoglobulin

Use of other class 5 fimbrial adhesins are also contemplated as eliciting protective passive antibody production. As a further illustration, results of inhibition by antibody to CS17 (i.e., CsbD) is presented in FIG. 5. The antigen used to elicit antibody was a CsbD polypeptide (SEQ ID No. 22) expressing construct. The construct was engineered similar to that for CfaE, in Example 1, above but with a nucleotide sequence encoding CsbD (SEQ ID No. 19). The construct was designated $dsc_{19}CsbD[His]_6$. The donor strand consisted of 19 amino acids of CsbA (SEQ ID No. 7).

Figure 5A:
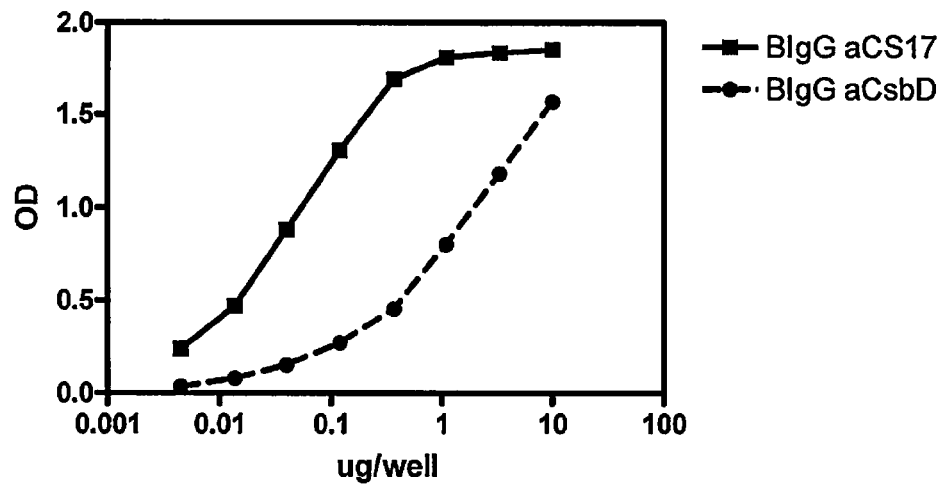
FIG. 5. Reactivity of products with a panel of CS17-related antigens by ELISA.
Figure 5B:
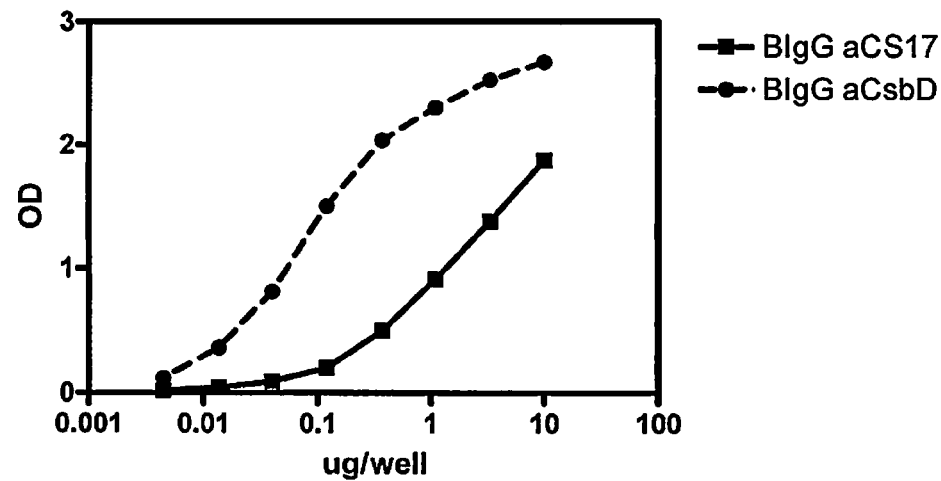

As can be seen in FIG. 5, like that for CfaE, antibody to CsbD was highly efficient at inhibiting MRHA. Also, like that observed for CfaE, anti-CsbD antibody also afforded cross-protection against CS4 and CS2.

Figure 6:
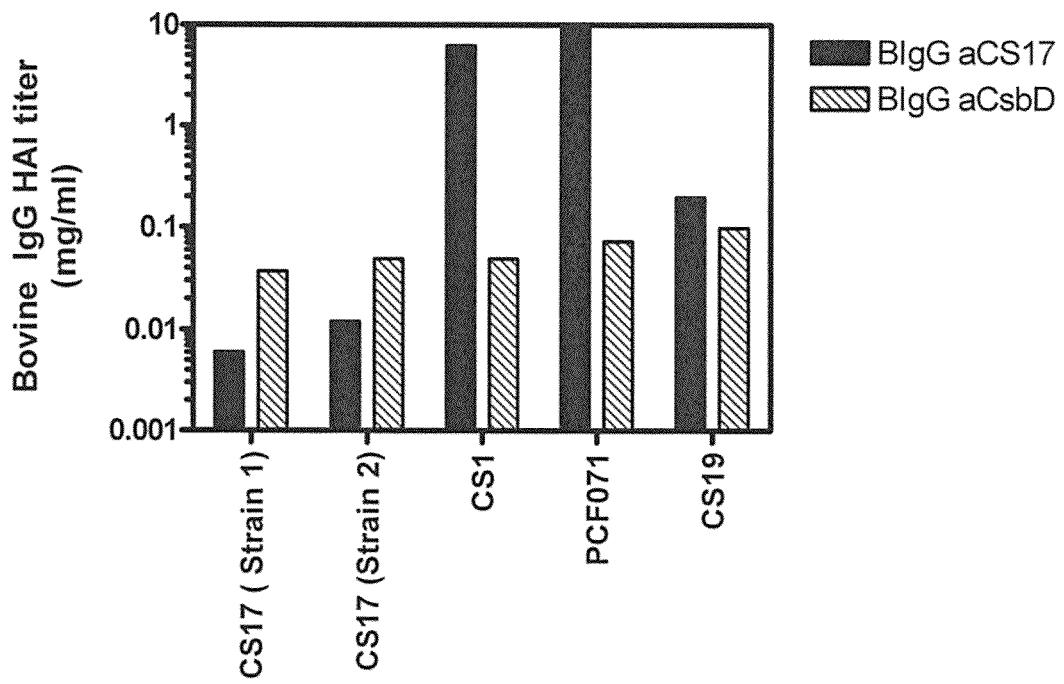
FIG. 6. In vitro functional activity of BIgG anti-CsbD.

The functional activity of BIgG to CS17 and CsbD was also evaluated, as in FIG. 4. These results are illustrated in FIG. 6. Like that observed for anti-CfaE and anti-CFA/I, BIgG against both CS17 and CsbD exhibited significant inhibitory activity. However, more pronounce than for anti-CfaE BIgG, anti-CsbD, compared to anti-CS17 BIgG, exhibited significant inhibitory activity even to heterologous antigens. These observations, along with that observed for CfaE indicate that only a limited number of species within the Class five adhesin genus is likely to be required for efficacious passive protection.

Example 3

Specific Regions of ETEC Fimbrial Adhesin are Important for Immunoreactivity and Stability Crystollgraphic analysis of the dscCfaE reveals that fimbrial adhesin is composed of two domains, an adhesin domain, formed by the amino-terminal segment of the adhesin molecule and a C-terminal pilin domain. The two domains are separated by a three amino acid linker. In an attempt to understand those regions of fimbrial adhesin, amino acid substitutions where made and the ensuing immunoreactivity analyzed. It was found that replacement of arginine 67 or arginine 181 with alanine, on CfaE abolishes the in vitro adherence phenotype of the molecule. These amino acids positions are located on exposed regions of the molecule with residue Arg 181 located on the distal portion of the amino-terminus of the domain. Therefore, this region of CfaE and the comparable region of the other fimbrial adhesins, is important for efficacious immune induction. Table 3 summarizes the positions in the eight adhesins. Also shown in Table 3 is that region of the domain that has added importance, based on crystollgraphic analysis, in conferring structural stability of the fimbrial adhesin molecule.

TABLE 3

| Fimbrial Adhesin | Fimbrial Adhesin domain residues important for immunoreactivity | Fimbrial Adhesin domain residues important for structural stability |
| --- | --- | --- |
| CfaE | amino acids 66-183 | amino acids 22-202 |
| CsuD | amino acids 66-183 | amino acids 22-202 |
| CsfD | amino acids 66-183 | amino acids 22-202 |
| CooD | amino acids 65-183 | amino acids 20-205 |
| CosD | amino acids 65-185 | amino acids 20-205 |
| CsbD | amino acids 65-183 | amino acids 20-205 |
| CsdB | amino acids 65-183 | amino acids 20-205 |
| CotD | amino acids 58-177 | amino acids 14-196 |

Stabilization of the adhesin domain of intact fimbrial adhesin molecules is provided by the major subunit. However, devoid of the pili domain, fimbrial adhesin exhibits greater conformational stability than the intact molecule with concomitant retention of immunoreactivity. As an alternative to administration of the intact adhesin molecule, administration of only the adhesin domain is an alternative immunogen for induction of anti-fimbrial adhesin antibodies. Therefore, as an example, recombinant adhesin domain constructs encoding CfaE, CsbD and CotD adhesin domains, but not containing the pili domain, were constructed, by polymerase chain reaction amplification of the adhesin domain and inserted into pET 24a™. The amino acid sequences of the recombinant product is illustrated in SEQ ID Nos. 35, 36 and 37. Incorporation of a polyhistidine tail, as in Example 1 and 2, facilitates purification of the ensuing expressed product.

Example 4

Administration of Anti-Fimbrial Adhesin as Prophylactic Against ETEC

Class five fimbrial adhesins can be used for the development of prophylactic protection against ETEC infection. Protection is provided by collecting colostrums or milk product from fimbrial adhesin, either native or recombinant *Escherichia coli* adhesin, immunizing cows. Immunization can be by any number of methods. However, a best mode is the administration of three doses intramuscularly three weeks apart with a final administration, 1 to 2 weeks prior to calving, of se in 1 to 2 ml volume containing up to 500 μg of said adhesin. Collection of milk or colostrums can be at anytime, however optimal results likely is when collection is 1 to 2 weeks prior to calving.

Administration of the anti-adhesin bovine immunoglobulin as a prophylactic is achieved by ingestion of 0.1 g IgG/dose to 20.0 g of IgG/dose. The anti-adhesin bovine colostrum or milk immunoglobulin can be ingested alone or mixed with a number of beverages or foods, such as in candy. The immunglobulin can also be reduced to tablet or capusular form and ingested.

REFERENCES

1. Black, R. E. 1990. Epidemiology of travelers' diarrhea and relative importance of various pathogens. Rev Infect Dis 12 (Suppl 1):S73-S79.
2. Huilan, S., L. G. Zhen, M. M. Mathan, M. M. Mathew, J. Olarte, R. Espejo, U. Khin Maung, M. A. Ghafoor, M. A. Khan, Z. Sami, and et al. 1991. Etiology of acute diarrhoea among children in developing countries: a multicentre study in five countries. Bull World Health Organ 69:549-55.
3. Nataro, J. P., and J. B. Kaper. 1998. Diarrheagenic *Escherichia coli*. Clin Microbiol Rev 11:142-201.
4. Gaastra, W., and A. M. Svennerholm. 1996. Colonization factors of human enterotoxigenic *Escherichia coli* (ETEC). Trends Microbiol 4:444-452.
5. Evans, D. G., R. P. Silver, D. J. Evans, Jr., D. G. Chase, and S. L. Gorbach. 1975. Plasmid-controlled colonization factor associated with virulence in *Escherichia coli* enterotoxigenic for humans. Infect Immun 12:656-667.
6. Grewal, H. M., H. Valvatne, M. K. Bhan, L. van Dijk, W. Gaastra, and H. Sommerfelt. 1997. A new putative fimbrial colonization factor, CS19, of human enterotoxigenic *Escherichia coli*. Infect Immun 65:507-513.
7. Khalil, S. B., F. J. Cassels, H. I. Shaheen, L. K. Pannell, K. A. Kamal, B. T. Pittner, M. Mansour, R. Frenck, S. J. Savarino, and P. L. F. 2000. Presented at the 100th General Meeting of the American Society for Microbiology, Los Angeles, Calif.
8. Froehlich, B. J., A. Karakashian, L. R. Melsen, J. C. Wakefield, and J. R. Scott. 1994. CooC and CooD are required for assembly of CS1 pili. Mol Microbiol 12:387-401.
9. Froehlich, B. J., A. Karakashian, H. Sakellaris, and J. R. Scott. 1995. Genes for CS2 pili of enterotoxigenic *Escherichia coli* and their interchangeability with those for CS1 pili. Infect Immun 63:4849-56.
10. Jordi, B. J. A. M., G. A. Willshaw, A. M. van der Zeijst, and W. Gaastra. 1992. The complete nucleotide sequence of region 1 of the CFA/I fimbrial operon of human enterotoxigenic *Escherichia coli*. DNA Seq 2:257-263.
11. Perez-Casal, J., J. S. Swartley, and J. R. Scott. 1990. Gene encoding the major subunit of CS1 pili of human enterotoxigenic *Escherichia coli*. Infect Immun 58:3594-3600.
12. Scott, J. R., J. C. Wakefield, P. W. Russell, P. E. Orndorff, and B. J. Froehlich. 1992. CooB is required for assembly but not transport of CS1 pilin. Mol Microbiol 6:293-300.
13. Gaastra, W., H. Sommerfelt, L. van Dijk, J. G. Kusters, A. M. Svennerholm, and H. M. Grewal. 2002. Antigenic variation within the subunit protein of members of the colonization factor antigen I group of fimbrial proteins in human enterotoxigenic *Escherichia coli*. Int J Med Microbiol 292:43-50.
14. Ramer, S. W., G. K. Schoolnik, C. Y. Wu, J. Hwang, S. A. Schmidt, and D. Bieber. 2002. The Type IV pilus assembly complex: Biogenic interactions among the bundle forming pilus proteins of enteropathogenic *Escherichia coli*. J Bacteriol 184:3457-65.
15. Soto, G. E., and S. J. Hultgren. 1999. Bacterial adhesins: common themes and variations in architecture and assembly. J Bacteriol 181:1059-1071.
16. Low, D., B. Braaten, and M. Van der Woude. 1996. Fimbriae, p. 146-157. In F. C. Neidhardt, R. Curtiss III, J. L.

Ingraham, E. C. C. Lin, K. B. Low, B. Magasanik, W. S. Reznikoff, M. Riley, M. Schaechter, and H. E. Umbarger (ed.), *Escherichia coli* and *Salmonella*: Cellular and Molecular Biology, 2nd ed, vol. Volume 1. ASM Press, Washington, D. C.
17. Sakellaris, H., and J. R. Scott. 1998. New tools in an old trade: CS1 pilus morphogenesis. Mol Microbiol 30:681-7.
18. Sakellaris, H., V. R. Penumalli, and J. R. Scott. 1999. The level of expression of the minor pilin subunit, CooD, determines the number of CS1 pili assembled on the cell surface of *Escherichia coli*. J Bacteriol 181:1694-7.
19. Buhler, T., H. Hoschutzky, and K. Jann. 1991. Analysis of colonization factor antigen I, an adhesin of enterotoxigenic *Escherichia coli* O78:H11: fimbrial morphology and location of the receptor-binding site. Infect Immun 59:3876-3882.
20. Sakellaris, H., G. P. Munson, and J. R. Scott. 1999. A conserved residue in the tip proteins of CS1 and CFA/I pili of enterotoxigenic *Escherichia coli* that is essential for adherence. Proc Natl Acad Sci, USA 96:12828-12832.
21. Anantha, Ravi P., A. L. McVeigh, L. H. Lee, M. K. Agnew, F. J. Cassels, D. A. Scott, T S. Whittam, and S. J. Savarino. 2004. Evolutionary and functional relationships of colonization factor antigen I and other class 5 adhesive fimbriae of enterotoxigenic *Escherichia coli*. Inf and Imm. 72: 7190-7201.
22. Viboud, G. I., M. M. McConnell, A. Helander, and A. M. Svennerholm. 1996. Binding of enterotoxigenic *Escherichia coli* expressing different colonization factors to tissue-cultured Caco-2 cells and to isolated human enterocytes. Microb Pathogen 21:139 147.
23. Kuehn M J, J. Heuser, S. Normark and S. J. Hultgren. 1992. P pili in uropathogenic *E. coli* are composite fibres with distinct fibrillar adhesive tips. Nature 356:252-5.
24. Sauer F G, K. Futterer, J. S. Pinkner, K. W. Dodson, S. J. Hultgren and G. Waksman. 1999. Structural basis of chaperone function and pilus biogenesis. Science 285:1058-61.
25. Choudhury D, A. Thompson, V. Stojanoff, et al. X-ray structure of the FimC-FimH chaperone-adhesin complex from uropathogenic *Escherichia coli*. Science 999; 285: 1061 6.
26. Barnhart M M, Pinkner J S, Soto G E, et al. From the cover: PapD-like chaperones provide the missing information for folding of pilin proteins. Proc. Natl. Acad. Sci. U.S.A. 2000; 97:7709-14.
27. Sakellaris H, D. P. Balding and J. R. Scott. 1996. Assembly proteins of CS1 pili of enterotoxigenic *Escherichia coli*. Mol. Microbiol. 21:529-41.
28. Krasan G P, Sauer F G, Cutter D, et al. Evidence for donor strand complementation in the biogenesis of *Haemophilus influenzae* haemagglutinating pili. Mol. Microbiol. 2000; 35:1335-47.
29. Zavialov A V, Kersley J, Korpela T, Zav'yalov V P, MacIntyre S and Knight S D. Donor strand complementation mechanism in the biogenesis of non-pilus systems. Mol. Microbiol. 2002; 45:983-995.
30. Tacket, C. O., G. Losonsky, H. Link, and M. M. Levine. 1988. Protection by milk immunoglobulin concentrate against oral challenge with enterotoxigenic *Escherichia coli*. N Engl J. Med. 318: 1240-1243.
31. Davidson, G. P., P. B. Whyte, E. Daniels, et al. 1989. Passive immunization of children with bovine colostrums containing antibodies to human rotavirus. Lancet 2: 709-712.
32. Tacket, C. O., S. B. Binion, E. Bostwick, G. Losonsky, M. J. Roy and R. Edelman. 1992. Efficacy of bovine milk immunoglobulin concentrate in preventing illness after *Shigella flexneri* challenge. Am J. Trop. Med. Hyg. 47:276-283.
33. Freedman, D. J. C. O. Tacket, A. Delehanty, D. R. Maneval, J. Nataro, and J. H. Crabb. 1998. Milk immunoglobulin with specific activity against purified colonization factor antigens can protect against oral challenge with enterotoxigenic *Escherichia coli*. J. Infect. Dis. 177:662-667.
34. Greenberg, P. D., J. P. Cello. 1996. Treatment of severe diarrhea caused by *Cryptosporidium parvum* with oral bovine immunoglobulin concentrate in patients with AIDS. J. Acquir Immune Defic Syndr Hum Retrovirol 13:348-354.
35. Okhuysen, P. C. C. L. Chappell, J. Crabb, L. M. Valdez, E. T. Douglass and H. L. DuPont. 1998. Prophylactic effect of bovine anti-*Cryptosporidium* hyperimmune colostrums immunoglobulin in healthy volunteers challenged with *Cryptosporidium parvum*. Clin. Infect. Dis 26:1324-1329.
36. Ruch, F. E., E. A. Acker. 1998. U.S. Pat. No. 5,747,031 to ImmuCell Corporation.

What is claimed is:

1. A method of producing an anti-enterotoxigenic *Escherichia coli* composition comprising the steps:
    a. administering to a milk producing domesticated animal an immunogen composed of one or more constructs comprising a Class five *Escherichia coli* fimbrial adhesion linked at its C-terminus to a linker which is operatively linked at its C-terminus to an *Escherichia coli* major fimbrial subunit; and
    b. collecting anti-adhesin immunoglobulin containing colostrum or milk from said domesticated animal.

2. The method of claim 1, wherein the concentration of anti-adhesin immunoglobulin in said collected colostrum or milk is adjusted to 0.1 g IgG per dose to 20.0 g of IgG per dose.

3. The method of claim 1, wherein said domesticated animal is a cow or goat.

4. The method of claim 1, wherein said immunogen also comprises one or more *Escherichia coli* major fimbrial subunit is CfaB.

5. The method of claim 1, wherein said immunogen is an *Escherichia coli* fimbrial adhesin domain and polyhistidine tail fusion polypeptide composed of the amino acid sequence selected from the group consisting of SEQ ID No. 35, SEQ ID No. 36 and SEQ ID No. 37.

6. The method of claim 1, wherein said *Escherichia coli* fimbrial adhesin is a monomer or polymer of adhesin polypeptides.

7. The method of claim 1, wherein said linker is composed of the amino acid sequence selected from the group consisting of SEQ ID No. 10, 12 and 13.

8. The method of claim 1, wherein said fimbrial adhesin is CfaE.

9. The method of claim 1, wherein said major fimbrial subunit is CfaB.

10. The method of claim 1, wherein said immunogen contains a polyhistidine tail linked at the C-terminus of said *Escherichia coli* major fimbrial subunit.

11. The method of claim 8, wherein said fimbrial adhesin is the amino acid sequence selected from the group consisting of SEQ ID No. 11, SEQ ID No. 22, SEQ ID No. 27, SEQ ID No. 28, SEQ ID No. 29, SEQ ID No. 30, SEQ ID No. 31, and SEQ ID No. 32.

12. The method of claim 8, wherein said CfaE is composed of the amino acid sequence of SEQ ID NO: 11 encoded by the nucleotide sequence of SEQ ID NO: 18.

13. The method of claim 8, wherein said *Escherichia coli* fimbrial adhesin is composed of amino acids 58-185 of the sequence selected from the group consisting of SEQ ID No. 11, SEQ ID No. 22, SEQ ID No. 27, SEQ ID No. 28, SEQ ID No. 29, SEQ ID No. 30, SEQ ID No. 31, SEQ ID No. 32.

14. The method of claim 8, wherein said *Escherichia coli* fimbrial adhesin is composed of amino acids 14-205 of the sequence selected from the group consisting of SEQ ID No. 11, SEQ ID No. 22, SEQ ID No. 27, SEQ ID No. 28, SEQ ID No. 29, SEQ ID No. 30, SEQ ID No. 31, SEQ ID No. 32.

15. The method of claim 9, wherein said major fimbrial subunit is the amino acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, and SEQ ID No. 9.

16. The method of claim 10, wherein said immunogen is a fusion polypeptide containing a polyhistidine tail composed of the amino acid sequence selected from the group consisting of SEQ ID No. 23 encoded by SEQ ID No. 24, SEQ ID No. 25 encoded by SEQ ID No. 26 and SEQ ID No. 34.

17. The method of claim 9, wherein said CfaB is a polypeptide sequence of SEQ ID NO: 1 encoded by nucleotide sequence of SEQ ID NO: 20.

* * * * *